United States Patent [19]

Thomas et al.

[11] Patent Number: 5,433,948

[45] Date of Patent: Jul. 18, 1995

[54] CLONING AND SEQUENCING OF ALLERGENS OF DERMATOPHAGOIDES (HOUSE DUST MITE)

[76] Inventors: Wayne R. Thomas, 31 Taylor Road, Nedlands, Australia, 6009; Kaw-Yan Chua, 35 Munja Way, Nollamara, Australia, 6061

[21] Appl. No.: 945,288

[22] Filed: Sep. 10, 1992

Related U.S. Application Data

[63] Continuation-in-part of Ser. No. 580,655, Sep. 11, 1990, abandoned, which is a continuation-in-part of Ser. No. 458,642, Feb. 13, 1990, abandoned.

[51] Int. Cl.$^6$ ............................................. C07K 19/00
[52] U.S. Cl. ............................ 424/185.1; 424/192.1; 424/200.1; 424/275.1; 514/12; 530/350
[58] Field of Search ............... 424/88, 91, 538, 185.1, 424/192.1, 200.1, 275.1; 530/350, 858; 436/547, 513, 826; 435/68.1, 69.1, 69.3, 69.7, 69.8, 71.1, 172.3, 252.3, 320.1; 514/12

[56] References Cited

U.S. PATENT DOCUMENTS 5,026,545  6/1991  Saint-Remy et al. ............... 424/85.8

FOREIGN PATENT DOCUMENTS

50598/90  2/1990  Australia .
71277/91  2/1991  Australia .

OTHER PUBLICATIONS

Chapman, et al., "II. Mite Allergens", The UCB Institute of Allergy, Bad Kreznach, Sep. 1-2, 1987.
Chua, et al., Abstract, *Chemical Abstracts*, vol. 105, p. 148, 1988.
Chua, et al., Abstract, "Expression of Dermatophagoides pteronyssinus Allergen, Der p II, in *Escherichia coli* and the Binding Studies with Human IgE", 1990, *Chemical Abstracts*, vol. 113, p. 434.
Chua, et al., "Isolation of cDNA Coding for the Major Mite Allergen Der p II by IgE Plaque Immunoassay", *International Arch. of Allergy & Applied Immunol.*, 1990, vol. 91, pp. 118-123.
Ford, et al., "The Spectrum of Low Molecular Weight House Dust Mite Allergens with Emphasis on Der p II", *Clin. and Exerimental Allergy, 1989, vol. 20, pp. 27-31.*
Gurka, et al., "Allergen-specific Human T Cell Clones: Derivation, Specificity, and Activation Requirements", *J. Allergy Clin. Immunol.*, May 1989, pp. 945-954.
Heymann, et al., "Antigen Der f I from theust mite Dermatophagoides Farinae: structural comparison with Der p I from Dermatophagoides Pteronyssinus and Epitope Specificity . . . antibodies", *The Journal of Immunol.*, vol. 9, pp. 2841-2847.
Krillis, et al., "Antigens and Allergens from the Common House Dust Mite . . . Dermatophagoides pteronyssinus", *Journal Aller. Clin, Immunol.*, Aug. 1984, pp. 142-146.
Lamb, et al., "The use of nitrocellulose immunoblots for the analysis of antigen recognition by T lymphocytes," *Journal of Immun. Methods*, 1988, vol. 110, pp. 1-16.
Lamb, et al., "HLA class II restriction specificity of Dermatophagoides spp. reactive T lymphocyte clones (List continued on next page.)

*Primary Examiner*—Christine M. Nucker
*Assistant Examiner*—Lautlie Scheiner

[57] ABSTRACT

The present invention features isolated DNA encoding allergens of Dermatophagoides (house dust mites) particularly of the species *Dermatophagoides farinae* and *Dermatophagoides pteronyssinus,* which are protein allergens or peptides which include at least one epitope of the protein allergen. In particular, the invention provides DNA encoding the major *D. farinae* allergens, *Der f* I and *Der f* II and DNA encoding the major *D. pteronyssinus* allergens, *Der p* I and *Der p* II. The present invention further relates to proteins and peptides encoded by the isolated *D. farinae* and *D. pteronyssinus* DNA, including proteins containing sequence polymorphisms. In addition, the proteins or peptides encoded by the isolated DNA, their use a diagnostic and therapeutic reagents and methods of diagnosing and treating sensitivity to house dust mite allergens, are disclosed.

2 Claims, 29 Drawing Sheets

OTHER PUBLICATIONS that support IgE synthesis", *Clin. and Experim. Allergy*, 1989, vol. 19, pp. 389–393.

O'Hehir, et al., "Clonal Analysis of the Cellular Immune Response to the House Dust Mite Dermatophagoides farinae", *Int. Arch. Allergy Appl. Immunol.*, 1989, vol. 88, pp. 170–172.

Pierce, et al., ABSTRACT, "Molecular cloning of Schistosoma", *Biochem. Genetics*, vol. 108, p. 191, 1986.

Rosenwasser, Lanny J., "Molecular Biology of Allergen Characterization, " Post Graduate Education Course Syllabus, AAAI Meeting, Mar. 5, 1991.

Schad, V. et al., "The Potential Use of T Cell EPitopes to Alter the Immune Response", *Immunology, vol. 3, 1991, pp. 217–224.*

Stewart, et al., "Immunogenicity and Tolerogenicity of a Major House Dust Mite Allergen, Der p I from Dermatophagoides pteronyssinus, in Mice and Rats", *Int. Archs. Allergy Appl. Immun.*, vol. 83, pp. 44–51, May 1987.

Stewart, et al., "In vitro Translation of Messenger RNA from the House Dust Mite", Aug. 1987, *Int. Archs. Allergy Appl. Immunol.*, vol. 83, pp. 384–389.

Stewart, et al., "An Allergen and Antigenic Mapping Analysis of a Major Mite Allergen, Der p I", Apr., 1988, DPC First International Symposium, Laguna Niguel, California.

Stewart, et al., ABSTRACT, Abstracts from the Annual Meeting, "The Physicochemical Characterization of a Major Protein Allergen from the House Dust Mite, Dermatophagoides pteronyssinus", p. 71.

Stewart, et a., "2. Epitope mapping analysis of the major mite allergens using synthetic peptides, " Meeting on Sep. 1987, (see International Workshop Report, 1988), Mite Allergy Conference, Bad Kreuznach.

Thomas, et al., "Cloning and Expression of DNA Coding for the Major House Dust Mite Allergen Der p I in *Esherichia coli*", *Int. Archs. Allergy Appl. Immun.* , vol. 85, 1988, pp. 127–129.

Thomas, et al., "4. Expression of the house dust mite allergen Der p I in *E. coli*", Mite Allergy Conference, BadKreuznach.

Thomas et al., "6. Recombinant Mite Allergens", Proc of Workshop XIV London Europe Acad. Allergy, Sep. 1989.

Thomas, et al., "Analysis and Expression of cDNA clones coding for house dust mite allergens", *Biochem. Genetics*, 1990, vol. 113, p. 179.

Tovey, et al., "Cloning and Sequencing of a cDNA Expressing a Recombinant House Dust Mite Protein . . . low molecular weight allergen", Brief Definitive Report, *J. Exp. Med.*, Oct. 1989, vol. 170, pp. 1457–1462.

Trudinger, et al., "cDNA endocing the major mite allergen Der f II," *Clinical and Exper. Allergy*, 1991, vol. 24, pp. 33–37.

Tasueda, et al., "Isolation and characterization of two allergens from Dermatophagoides farinae", *Chemical Abstracts*, ABSTRACT, vol. 105, p. 552.

Yssel, et al., "T cell activation by allergen derived synthetic peptides", Session 4: Immunity to Peptides, Sep. 24, 1990, Trinity College, Oxford, U.K.

Yukki, et al., "Cloning and Sequencing of cDNAs Corresponding to mite major allergen Der f II", *Jpn J. Allergio*, 39, (6), 557–561, 1990.

Yssel, et al., "T cell activation–inducing epitopes of the house dust mite allergen Der p I", *The Journal of Immunology*, vol. 148, Feb. 1992, pp. 738–745.

Greene, et al., "IgE Binding Structures of the Major House Dust Mite Allergen Der p I", *Molecular Immunology*, vol. 29, No. 2, pp. 257–262, 1992.

Chua, et al., "IgE binding studies with large peptides expressed from der p II cDNA constructs", *Clinical and Experimental Allergy*, 1991, vol. 21, pp. 161–166.

Van't Hof, et al., "Epitope mapping of the dermatophagoides pteromyssinus house dust mite major allergen Der p II using overlapping synthetic peptides", Molecular Immunology, vol. 28, No. 11, 1991, pp. 1225–1232.

Greene, et al., "IgE and EgG binding of peptides expressed from fragments of cDNA encoding the major house dust mite allergen der p I", *The Journal of Immunol.*, vol. 147, Dec. 1991, pp. 3768–3773.

| | | | | | | | | | | | | | | | | |
|---|---|---|---|---|---|---|---|---|---|---|---|---|---|---|---|---|
| -23 | | | | | | | | | -10 | | | | | | | |
| AAA | AAC | CGA | TTT | TTG | ATG | AGT | GCA | GAA | GCT | TTT | GAA | CAC | CTC | AAA | ACT | 48 |
| Lys | Asn | Arg | Phe | Leu | Met | Ser | Ala | Glu | Ala | Phe | Glu | His | Leu | Lys | Thr | |
| | | | | | | -1 | 1 | | | | | | | | | |
| CAA | TTC | GAT | TTG | AAT | GCT | GAA | ACT | AAC | GCC | TGC | AGT | ATC | AAT | GGA | AAT | 96 |
| Gln | Phe | Asp | Leu | Asn | Ala | Glu | Thr | Asn | Ala | Cys | Ser | Ile | Asn | Gly | Asn | |
| | 10 | | | | | | | | | 20 | | | | | | |
| GCT | CCA | GCT | GAA | ATC | GAT | TTG | CGA | CAA | ATG | CGA | ACT | GTC | ACT | CCC | ATT | 144 |
| Ala | Pro | Ala | Glu | Ile | Asp | Leu | Arg | Gln | Met | Arg | Thr | Val | Thr | Pro | Ile | |
| | | | 30 | | | | | | | | | | | 40 | | |
| CGT | ATG | CAA | GGA | GGC | TGT | GGT | TCA | TGT | TGG | GCT | TTC | TCT | GGT | GTT | GCC | 192 |
| Arg | Met | Gln | Gly | Gly | Cys | Gly | Ser | Cys | Trp | Ala | Phe | Ser | Gly | Val | Ala | |
| | | | | | | | | 50 | | | | | | | | |
| GCA | ACT | GAA | TCA | GCT | TAT | TTG | GCT | CAC | CGT | AAT | CAA | TCA | TTG | GAT | CTT | 240 |
| Ala | Thr | Glu | Ser | Ala | Tyr | Leu | Ala | His | Arg | Asn | Gln | Ser | Leu | Asp | Leu | |
| | | 60 | | | | | | | | | | 70 | | | | |
| GCT | GAA | CAA | CAA | TTA | GTC | GAT | TGT | GCT | TCC | CAA | CAC | GGT | TGT | CAT | GGT | 288 |
| Ala | Glu | Gln | Gln | Leu | Val | Asp | Cys | Ala | Ser | Gln | His | Gly | Cys | His | Gly | |
| | | | | 80 | | | | | | | | | | | | |
| GAT | ACC | ATT | CCA | CGT | GGT | ATT | GAA | TAC | ATC | CAA | CAT | AAT | GGT | GTC | GTC | 336 |
| Asp | Thr | Ile | Pro | Arg | Gly | Ile | Glu | Tyr | Ile | Gln | His | Asn | Gly | Val | Val | |
| | 90 | | | | | | | | 100 | | | | | | | |
| CAA | GAA | AGC | TAC | TAT | CGA | TAC | GTT | GCA | CGA | GAA | CAA | TCA | TGC | CGA | CGA | 384 |
| Gln | Glu | Ser | Tyr | Tyr | Arg | Tyr | Val | Ala | Arg | Glu | Gln | Ser | Cys | Arg | Arg | |
| | | | | 110 | | | | | | | | | | 120 | | |
| CCA | AAT | GCA | CAA | CGT | TTC | GGT | ATC | TCA | AAC | TAT | TGC | CAA | ATT | TAC | CCA | 432 |
| Pro | Asn | Ala | Gln | Arg | Phe | Gly | Ile | Ser | Asn | Tyr | Cys | Gln | Ile | Tyr | Pro | |
| | | | | | | 130 | | | | | | | | | | |

FIG. 1A

```
CCA AAT GCA AAC AAA ATT CGT GAA GCT TTG GCT CAA ACC CAC AGC GCT 480
Pro Asn Ala Asn Lys Ile Arg Glu Ala Leu Ala Gln Thr His Ser Ala
        140                         150

ATT GCC GTC ATT ATT GGC ATC ATT AAA GAT TTA GAC GCA TTC CGT CAT TAT 528
Ile Ala Val Ile Ile Gly Ile Ile Lys Asp Leu Asp Ala Phe Arg His Tyr
                    160

GAT GGC CGA ACA ATC ATT CAA CGC GAT AAT GGT TAC CAA CCA AAC TAT 576
Asp Gly Arg Thr Ile Ile Gln Arg Asp Asn Gly Tyr Gln Pro Asn Tyr
170                                 180

CAC GCT GTC AAC ATT GTT GGT TAC AGT AAC GCA CAA GGT GTC GAT TAT 624
His Ala Val Asn Ile Val Gly Tyr Ser Asn Ala Gln Gly Val Asp Tyr
            190                                     200

TGG ATC GTA CGA AAC AGT TGG GAT ACC AAT TGG GGT GAT AAT GGT TAC 672
Trp Ile Val Arg Asn Ser Trp Asp Thr Asn Trp Gly Asp Asn Gly Tyr
                        210

GGT TAT TTT GCT GCC AAC GAT TTG ATG ATG ATT GAA GAA TAT CCA 720
Gly Tyr Phe Ala Ala Asn Ile Asp Leu Met Met Ile Glu Glu Tyr Pro
        220

TAT GTT GTC ATT CTC TAAACAAAAAAGACAATTTCTTATATGATTGTCACTAATTTATT 778
Tyr Val Val Ile Leu
222

TAAAATCAAAATTTTAGAAAAATGAATAAATTCATTCACAAAAATTAAAAAAAAAAAAAAAAA 841
AAAAAAAAAAAAAAAAA 857
```

FIG. 1B

```
Der p  1  Thr Asn Ala Cys Ser Ile Asn  -  Gly Asn Ala Pro
                                              10
Der f  1  Thr Ser Ala Cys Arg Ile Asn Ser Val Asn Val Pro

Der p  1  Ala Glu Ile Asp Leu Arg Gln Met
                                  20
Der f  1  Ser Glu Leu Asp Leu Arg Ser Leu
```

FIG.3.

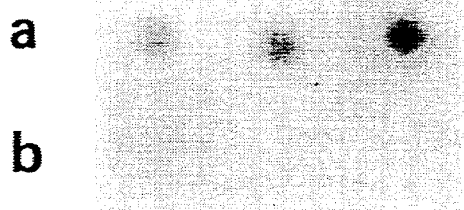 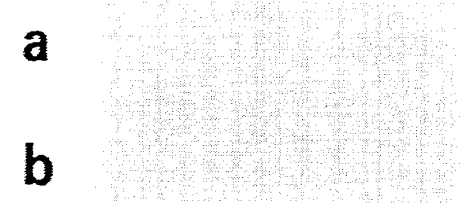
FIG. 4

CACAAATTCTTCTTCTTCCTTACTACTGATCATTAATCTGAAAACAAAACCAAACAAACCAT

```
       -16
TCAAAATGATG TAC AAA ATT TTG TGT CTT TCA TTG TTG GTC GCA GCC GTT
            Met Tyr Lys Ile Leu Cys Leu Ser Leu Leu Val Ala Ala Val
                                       -10
   -1   1
GCT CGT GAT CAA GTC GAT GTC AAA GAT TGT GCC AAT CAT GAA ATC AAA
Ala Arg Asp Gln Val Asp Val Lys Asp Cys Ala Asn His Glu Ile Lys
                                                10

AAA GTT TTG GTA CCA GGA TGC CAT GGT TCA GAA CCA TGT ATC ATT CAT
Lys Val Leu Val Pro Gly Cys His Gly Ser Glu Pro Cys Ile Ile His
                20                                          30

CGT GGT AAA CCA TTC CAA TTG GAA GCC GTT TTC GAA GCC AAC CAA AAC
Arg Gly Lys Pro Phe Gln Leu Glu Ala Val Phe Glu Ala Asn Gln Asn
                            40

ACA AAA ACG GCT AAA ATT GAA ATC AAA GCC TCA ATC GAT GGT TTA GAA
Thr Lys Thr Ala Lys Ile Glu Ile Lys Ala Ser Ile Asp Gly Leu Glu
            50                                  60
```

FIG. 7A

```
GTT GAT GTT CCC GGT ATC GAT CCA AAT GCA TGC CAT TAC ATG AAA TGC
Val Asp Val Pro Gly Ile Asp Pro Asn Ala Cys His Tyr Met Lys Cys
                        70
     80
CCA TTG GTT AAA GGA CAA CAA TAT GAT ATT AAA TAT ACA TGG AAT GTT
Pro Leu Val Lys Gly Gln Gln Tyr Asp Ile Lys Tyr Thr Trp Asn Val
                    100                 90
                                                            110
CCG AAA ATT GCA CCA AAA TCT GAA AAT GTT GTC ACT GTT AAA GTT
Pro Lys Ile Ala Pro Lys Ser Glu Asn Val Val Thr Val Lys Val

ATG GGT GAT GAT GGT GTT TTG GCC TGT GCT ATT GCT ACT CAT GCT AAA
Met Gly Asp Asp Gly Val Leu Ala Cys Ala Ile Ala Thr His Ala Lys
                            120

ATC CGC GAT TAAATCAAACAAAAATTTATTGATTTTGTAATCACAAATGATTGATTTTCTT
Ile Arg Asp
    129

TCCAAAAAAAAATAAATAAATTTTGGGAATTC  581
```

FIG. 7B

Der p II    DQVDVKDCANHEIKKVLVPGCHGSEPCIIHRGKPF
              •   • •         •

Der f II    DQVDVKD?ANNEIKKVMVDG?HGSDP?IIHRGKPF

• - non homologous residues.

Fig.8.

```
                                                                                    -98
GAATTCGTTTCTTCCATCAAATTAAAAATTCATCAAA ATG AAA TTC GTT TTG GCC ATT          62
                                      Met Lys Phe Val Leu Ala Ile
                                      -80
GCC TCT TTG TTG GTA TTG AGC ACT GTT TAT GCT CGT CCA GCT TCA ATC AAA ACT    116
Ala Ser Leu Leu Val Leu Ser Thr Val Tyr Ala Arg Pro Ala Ser Ile Lys Thr
-70                                            -60
TTT GAA TTC AAA AAA GCC TTC GCA AAC TAT AAC GTT GAA GAG GAA                170
Phe Glu Phe Lys Lys Ala Phe Ala Asn Tyr Asn Val Glu Glu Glu
         -50
GAA GTT GCC CGT AAA AAC TTT TTG TCA TTG GAA CTC TAT GTT GAA GCT AAC AAA    224
Glu Val Ala Arg Lys Asn Phe Leu Ser Leu Glu Leu Tyr Val Glu Ala Asn Lys
           -30                                                  -20
GGT GCC ATC AAC CAT TTG TCC GAT TTG TCA GAT CTC GAA TTC AAA AAC CGT TAT    278
Gly Ala Ile Asn His Leu Ser Asp Leu Ser Asp Leu Glu Phe Lys Asn Arg Tyr
TTG ATG AGT GCT GAA GCT TTT GAA CAA CTC CAA CTC AAA ACT CAA TTC GAT TTG AAT GCC   332
Leu Met Ser Ala Glu Ala Phe Glu Gln Leu Gln Leu Lys Thr Gln Phe Asp Leu Asn Ala
-1   1                                            10
GAA ACA AGC GCT TGC CGT ATC AAT TCG GTT AAC GTT CCA TCG GAA TTG GAT TTA    386
Glu Thr Ser Ala Cys Arg Ile Asn Ser Val Asn Val Pro Ser Glu Leu Asp Leu
         20                                           30
CGA TCA CTG CGA ACT GTC ACT CCA ATC CGT ATG CAA GGA TGT GGT TCA TGT        440
Arg Ser Leu Arg Thr Val Thr Pro Ile Arg Met Gln Gly Cys Gly Ser Cys
         40                                           50
TGG GCT TTC TCT GGT GTT GCC ACT GAA TCA GCT TAT TTG GCC TAC CGT AAC        494
Trp Ala Phe Ser Gly Val Ala Thr Glu Ser Ala Tyr Leu Ala Tyr Arg Asn
```

```
ACG TCT TTG GAT CTT TCT GAA CAG GAA CTC GTC GAT TGC GCA TCT CAA CAC GGA   548
Thr Ser Leu Asp Leu Ser Glu Gln Glu Leu Val Asp Cys Ala Ser Gln His Gly
                        60                              70

TGT CAC GGC GAT ACA ATA CCA AGA GGC ATC GAA TAC ATC CAA AAT GGT GTC       602
Cys His Gly Asp Thr Ile Pro Arg Gly Ile Glu Tyr Ile Gln Asn Gly Val
 90                             80

GTT GAA GAA AGA AGC TAT CCA GTT GCA GAA CGA CAA CGA TGC CGA CGA CCA       656
Val Glu Glu Arg Ser Tyr Pro Val Ala Glu Arg Gln Arg Cys Arg Arg Pro
        110                                     120

AAT TCG CAA CAT TAC TCA AAC TAC TGC CAA ATT TAT CCA CCA GAT GTG           710
Asn Ser Gln His Tyr Ser Asn Tyr Cys Gln Ile Tyr Pro Pro Asp Val
            130                                 140

AAA CAA ATC CGT GAA GCT TTG ACT CAA CAC ACA GCT ATT GCC GTC ATT ATT       764
Lys Gln Ile Arg Glu Ala Leu Thr Gln His Thr Ala Ile Ala Val Ile Ile
                150                                     160

GGC ATC AAA GAT TTG AGA GCT TTC CAA CAT TAT CAT GCC CGA ACA ATC CAA       818
Gly Ile Lys Asp Leu Arg Ala Phe Gln His Tyr His Ala Arg Thr Ile Gln
                        170

CAT GAC AAT GGT TAT CAA CCA AAC TAT CAT GCC GTC AAC ATT GTC GGT TAC GGA   872
His Asp Asn Gly Tyr Gln Pro Asn Tyr His Ala Val Asn Ile Val Gly Tyr Gly
180                                             190

AGT ACA CAA GGC GAC GAT TAT TGG ATC GTA CGA AAC AGT TGG GAT ACT ACC TGG   926
Ser Thr Gln Gly Asp Asp Tyr Trp Ile Val Arg Asn Ser Trp Asp Thr Thr Trp
            200                                         210

GGA GAT AGC GGA TAC GGA TAT TTC CAA GCC GGA AAC CTC ATG ATG ATC GAA       980
Gly Asp Ser Gly Tyr Gly Tyr Phe Gln Ala Gly Asn Leu Met Met Ile Glu
                220  223

CAA TAT CCA TAT GTT GTA ATC ATG TGAACATTTGAAATTGAATATATTTATTGTTTCAAAAT   1044
Gln Tyr Pro Tyr Val Val Ile Met
AAAACAACTACTCTTGGAGTATTTTTACTCGGAATTC 1084
```

FIG. 12A

```
Cathepsin H    MWTALPLLCAGAWLLSAGATA--------------------------------ELTY-NA-IEKFH-----FTSWMKQHQKTY-SS-
Cathepsin L    MTPLLLAVLCLFVAICLGTALA-------------------------------TPKFDQ-TF-NAQWH-----QWKSTHRRLY-GT-
Papain         MAMIPSISKLLFVAICLFVYMGLSFG---------------------DFSIVGYSQNDLTS-TE-RLIQL--FESWMLKHNKIYKNI--
Aleurain       MAHARVLLLALAVLATAAVAYASSSSFADSNPIRPVTDRAASTLESAVLGALGRTRHALRFARFAVRYGKSYESA-
CP1                     MKVILLFVLAVFTVF-------------------------------VSSRGIPPEEQ-SQ-FLEFQ-----DKFNKKYSHEEY-LE-
CP2                     MRLLVFLILIFVNFSFA-----------------------------NVRPNGRRFS-ES-QYRTA-----FTEWTLKFNRQY-SS-
Cathepsin B    MWWSLIPLSCLLALTSA-----------------------------------------------------------HDK---PS-
CTLA-2α        MVSICEQKLQHFSAVFLLILCLGMMSA--------------------------------APPPDPSLDNEWKEWKTKFAKAYNLN-
CTLA-2β        MVSICEQKLQHFSAVFLLILCLGMMSA--------------------------------APSPDPSLDNEWKEWKTTFAKAYSLD-
MCP                    NLLLAVLCLGTALA----------------------------------TPKFDQTFSAEWHQWKSTHRRLY-GT-
Der f I                 MKFVLAIASLLVLSTVYA-------------------------------RPASIKTFEEFKKAFNKNYATVE
                                                                                                  *   *
                                                                                                  **
```

```
Cathepsin H   REYSIIRLQVFANNWRKIQAHN--QRN--HTFKMG---LNQFSDMSFAEIKIKYL-WSE-PQNCS---AT-KS--NYL--RGTCP
Cathepsin L   NEEEWRRAVWEKNMRMIQIHNGEYSNGKHGFIHE--MNAFGDMTNEEFRQIVN-GYR-HQKHK--KG-RL--FQE--PLMLQ
Papain        DEKIYRFEIFKDNLKYIDETN--KKN--NSYWLG--LNVFADMSNDEFKEKYT-GSI-AGNYT--TTELSYEEVL-NDGDVN
Aleurain      AEVRRRFRIFSESLEEVRSTN--RKG--LPYRLG--INRFSDMSWEEFQATRL-GA--AQTCS--ATLAG--NHL-MRDAAA
CP1           RFEIFKSNLGKIFEELNLIAIN--HKA--DT-KFG--VNKFADLSSDEFKNYYLNNKEAIFTDD--LP-VA--DYLDDEFINS
CP2           SEFSNRYSIFKSNMDYVDNWN-SKGD--SQTVLG--LNNFADITNEEYRKTYL-GTR-VNAHSYNGYDGR--EVLNVEDLQT
Cathepsin B   ---FHPLS---DDM--INYIN--KQN--TTWQAG--RN-EYNV-DISYLKKPC-GTV-LGGPK--LP-ER---VGF--SEDIN
CTLA-2α       NEERHRRLVWEENKKIEAHNADYEQGKTSFYMG--LNQFSDLTPEEFKTNCY-GNSLNRGEM
CTLA-2β       DEERHRRLMWEENKKIEAHNADYERGKTSFYMG--LNQFSDLTPEEFRTNCC-GSSMCRGEM
MCP           NEEEWRRAIWEKNMRMIQLHNGEYSNGQHGFSME--MNAFGDMTNEEFRQVVN-GYRHQKHKK
Der p I                     ---KNRFL-MS--AEAFEH-L-KTQFRLNAE
                                 *    **  *         *
Actinidin     LRFIDEHNAD-TNR--SYKVG--LNQFADLTGEEFRSTYL-G
Der f I       EEEVARKN--FLESLKYVEA-NKGAINHLSDLSLDEFKNRYL-MS--AEAFEQ-L-KTQFDLNAE
              * *         *                        *    **  *         *
```

FIG. 12B

Der p1

Der f1

FIG. 14

```
GAT CAA GTC GAT GTT AAA GAT TGT GCC AAC AAT GAA ATC AAA AAA GTA ATG      51
Asp Gln Val Asp Val Lys Asp Cys Ala Asn Asn Glu Ile Lys Lys Val Met
                 10

GTC GAT GGT TGC CAT GGT TCT GAT CCA TGC ATC ATC CAT CGT GGT AAA CCA     102
Val Asp Gly Cys His Gly Ser Asp Pro Cys Ile Ile His Arg Gly Lys Pro
        20                              30

TTC ACT TTG GAA GCC TTA TTC GAT GCC AAC CAA AAC ACT AAA ACC GCT AAA     153
Phe Thr Leu Glu Ala Leu Phe Asp Ala Asn Gln Asn Thr Lys Thr Ala Lys
                        40                              50

ACT GAA ATC AAA GCC AGC CTC GAT GGT CTT GAA ATT GAT GTT CCC GGT ATT     204
Thr Glu Ile Lys Ala Ser Leu Asp Gly Leu Glu Ile Asp Val Pro Gly Ile
                                60

GAT ACC AAT GCT TGC CAT TTT ATG AAA TGT CCA TTG GTT AAA GGT CAA CAA     255
Asp Thr Asn Ala Cys His Phe Met Lys Cys Pro Leu Val Lys Gly Gln Gln
        70                              80

TAT GAT GCC AAA TAT ACA TGG AAT GTG CCG AAA ATT GCA CCA AAA TCT GAA     306
Tyr Asp Ala Lys Tyr Thr Trp Asn Val Pro Lys Ile Ala Pro Lys Ser Glu
                        90                             100

AAC GTT GTC GTT ACA GTC AAA CTT GTT CTT GTT GGT GAT AAT GGT GTT TTG GCT TGC   357
Asn Val Val Val Thr Val Lys Leu Val Leu Val Gly Asp Asn Gly Val Leu Ala Cys
                       110

GCT ATT GCT ACC CAC CGT AAA ATC CGT GAT TAAAAAAAAAATAATATGAAATT          414
Ala Ile Ala Thr His Ala Lys Ile Arg Asp
120                       129

TTCACCAACATCGAACAAATTCAATAACCAAAATTTGAATCAAAACGGAATTCCAGCTGAGCGC        481

CGGTCGCTAC                                                              491
```

FIG. 16A

```
Dp II:  CACAAATTCTTCTTCTTCCTTACTACTGATCATTAATCTGAAAACAAACCAAACAAACCAT                                              63

-16                                      -10
Dp II:  TCAAAATGATG TAC AAA ATT TTG TGT CTT TCA TTG TTG GTC GCA GCC GTT                                          113
                   Met Tyr Lys Ile Leu Cys Leu Ser Leu Val Ala Ala Val

-1   1
Dp II:  GCT CGT GAT CAA GTC GAT GTC AAA GAT TGT GCC AAT CAT GAA ATC AAA                                          161
        Ala Arg Asp Gln Val Asp Val Lys Asp Cys Ala Asn His Glu Ile Lys

Df II:                                    ..T ...   ...   ...   ...  ..C A.. ...  ...                            42
                                                                     Asn

30
Dp II:  AAA GTT TTG GTA CCA GGA TGC CAT GGT TCA GAA CCA TGT ATC ATT CAT                                          209
        Lys Val Leu Val Pro Gly Cys His Gly Ser Glu Pro Cys Ile Ile His

Df II:  ...  ..A A.. ..C GAT ..T ...   ...   ...   ..T ...  ...   ...   ..C ...   ...                            90
                    Met Asp                              Asp

40
Dp II:  CGT GGT AAA CCA TTC CAA TTG GAA GCC GTT TTC GAA GCC AAC CAA AAC                                          257
        Arg Gly Lys Pro Phe Gln Leu Glu Ala Val Phe Glu Ala Asn Gln Asn

Df II:  ...  ...   ...   ...   ACT ...   ...   ...   ...   ...   T.A ...  ...   ...  ..T  ...                   138
                              Thr                                 Leu                       Asp
```

FIG. 16B

```
Dp II:  ACA AAA ACG GCT AAA ATT GAA AAA GCC TCA ATC GAT GGT TTA GAA    305
        Thr Lys Thr Ala Lys Ile Glu Lys Ala Ser Ile Asp Gly Leu Glu
                     50                          60
Df II:  ... ..T ... ..C ... ... ... ... AGC C.. ... ... ... C.T ...    186
                                        Leu

Dp II:  GTT GAT GTT CCC GGT ATC GAT CCA AAT GCA TGC CAT TAC ATG AAA TGC  353
        Val Asp Val Pro Gly Ile Asp Pro Asn Ala Cys His Tyr Met Lys Cys
                                     70
Df II:  A.. ... ... ... ... ... ..T ... ... ... ..T ... ... ... ... .TT  234
        Ile                                                          Phe

Dp II:  CCA TTG GTT AAA GGA CAA CAA TAT GAT ATT AAA TAT ACA TGG AAT GTT  401
        Pro Leu Val Lys Gly Gln Gln Tyr Asp Ile Lys Tyr Thr Trp Asn Val
                 80                              90
Df II:  ... ... ... ... ... ... ... ... ... ... ..T ... ... ... ... ..G  282
                                                                     Ala
                                                    GCC

Dp II:  CCG AAA ATT GCA CCA AAA TCT GAA AAT GTT GTC ACT GTT AAA GTT      449
        Pro Lys Ile Ala Pro Lys Ser Glu Asn Val Val Thr Val Lys Val
                                 100                     110
Df II:  ... ... ... ... ... ... ... ... ... ... ..T ..A ..C ... C..     330
                                                                    Leu
```

FIG. 16C

```
                                                                                120
Dp II:  ATG GGT GAT GAT GGT GTT TTG GCC TGT GCT ATT GCT ACT CAT GCT AAA         497
        Met Gly Asp Asp Gly Val Leu Ala Cys Ala Ile Ala Thr His Ala Lys

Df II:  G.T ... ... A.. ... ... ... ..T ... ... ... ..C ... ..C ... ...         378
            Val

129
Dp II:  ATC CGC GAT TAA ATCAAACAAAATTTATTGATTTTGTAATCACAAATGATTGATTTCTT          557
        Ile Arg Asp END

Df II:  ... ... ..T ... ... ... AA...A...TAAATA...AAA.T.TCA.CA.C.CGAAC.AAA.TCA  438

Dp II:  TCCAAAAAAAAAATAAATAAAATTTGGGAATTC                                       591

Df II:  ATA.CC...TTTG..TC....AC____GGAATTC                                      469
```

```
                         10         20         30         40         50         60
Der p I (a)    TNACSINGNA PAEIDLRQMR TVTPIRMQGG CGSCWAFSGV AATESAYLAH RNQSLDLAEQ.
Der p I (b)    ---------- ---------- ---------- ---------- -------Y-- ----------
Der p I (c)    ---------- ---------- ---------- ---------- -------Y-- ----------
Der p I (d)    ---------- ---------- ---------- ---------- ---------- ----------

70         80         90        100        110        120
Der p I (a)    ELVDCASQHG CHGDTIPRGI EYIQHNGVVQ ESYYRYVARE QSCRRPNAQR FGISNYCQIY
Der p I (b)    --V------- ---------- K--------- ---------- ---------- ----------
Der p I (c)    --V------- ---------- ---------- ---------- ---------- ----------
Der p I (d)    ---------- ---------- ---------- ---------- ---------- ----------

130        140        150        160        170        180
Der p I (a)    PPNANKIREA LAQTHSAIAV IIGIKDLDAF RHYDGRTIIQ RDNGYQPNYH AVNIVGYSNA
Der p I (b)    ---------- ---------- ---------- ---------- ---------- ----------
Der p I (c)    ---------- ---------- ---------- ---------- ---------- ----------
Der p I (d)    ---------- ----T----- ---------- ---------- ---------- ----------
Der p I (e)    ---------- ---------- ---------- ---------- ---------- ----------

190        200        210        220
Der p I (a)    QGVDYWIVRN SWDTNWGDNG YGYFAANIDL MMIEEYPYVV IL
Der p I (b)    ---------- ---------- ---------- ---------- --
Der p I (c)    ---------- ---------- ---------- --Q------- --
Der p I (d)    ---------- ---------- ---------- ---------- --
Der p I (e)    ---------- ---------- ---------- ---------- --
```

FIG. 18

```
                    10         20         30         40         50
Der p II (c) DQVDVKDCANHEIKKVLVPGCHGSEPCIIHRGKPFQLEAVFEANQNTKTAK
         (1) ..........H......L.P.....E..........Q...V.E....T.
         (2) ..........H......L.P.....E..........Q...V.E....S.
Der f II     .........N.......M.D.....D..........T...L.D....T.

60         70         80         90        100
Der p II (c) IEIKASIDGLEVDVPGIDPNACHYMKCPLVKGQQYDIKYTWNVPKIAPKSE
         (1) .........I.............P....YM..........I........
         (2) .........I.............P....YM..........I........
Der f II     .........L.............T....FM..........A........
                                                      I 110        120
Der p II (c) NVVVTVKVMGDDGVLACAIATHAKIRD
         (1) .......VM.DD........A....I..
         (2) .......VM.ND........A....L..
Der f II     .......LV.DN........A....I..
                    I              G
```

FIG. 19

```
         10         20         30         40         50         60
         DQVDVKDCANNEIKKVMVPGCHGSEPCIIHRGKPFTLEALFDANQNTKTAKIEIKASLDGLE
pFL1     ............................................................
pFL2     .........N..................................................
MT 3     .........N...............................I.I...............
MT 5 (1-92) ......S...................................H.T...............
MT18 (1-84) ......N...................................H.I...............
MT16 (1-70) ......N.................................T.I...............

70         80         90        100        110        120       130
         IDVPGIDTNACHFVKCPLVKGQQYDIKYTWNVPKIAPKSENVVVTVKLIGDNGVLACAIATHAKIRD
pFL1     ..................................................................
pFL2     ...........M..........A...........................V..............
MT 3     ...........M..........A...........................V..............
MT 5     ...........M..........I...........................................
MT18     ...........M.......................................................
```

FIG. 20

```
GAATTCCTTT TTTTTCTTT CTCTCTCTAA AATCTAAAAT CCATCCAAC ATG AAA ATT                                              58
                                                     Met Lys Ile
                                                         -98

GTT TTG GCC ATC GCC TCA TTG TTG GCA TTG AGC GCT GTT TAT GCT CGT                                              106
Thr Leu Ala Ile Ala Ser Leu Leu Ala Leu Ser Ala Val Tyr Ala Arg
-95                 -90                 -85                 -80

CCA TCG ATC AAA ACT TTT GAA GAT CAA GAA TAC AAA AAA GCC TTC AAC AAA                                          154
Pro Ser Ile Lys Thr Phe Glu Asp Gln Glu Tyr Lys Lys Ala Phe Asn Lys
        -75                 -70                 -65

AGT TAT GCT ACC TTC GAA GAT CAA GAA GAT GCT GCC CGT AAA AAC TTT TTG                                          202
Ser Tyr Ala Thr Phe Glu Asp Gln Glu Asp Ala Ala Arg Lys Asn Phe Leu
    -60                 -55                 -50

GAA TCA GTA AAA TAT GTT CAA TCA AAT GGA GGT GCC ATC AAC CAT TTG                                              250
Glu Ser Val Lys Tyr Val Gln Ser Asn Gly Gly Ala Ile Asn His Leu
-45                 -40                 -35

TCC GAT TTG TCG TTG GAT GAA TTC AAA AAC CGA TTT TTG ATG AGT GCA                                              298
Ser Asp Leu Ser Leu Asp Glu Phe Lys Asn Arg Phe Leu Met Ser Ala
    -30                 -25                 -20

GAA GCT TTT GAA CAC CTC AAA ACT CAA TTC GAT TTG AAT GCT GAA ACT                                              346
Glu Ala Phe Glu His Leu Lys Thr Gln Phe Asp Leu Asn Ala Glu Thr
-15                 -10                 -5                   -1  1

AAC GCC TGC AGT ATC AGT ATC AAT GGA AAT GCT CCA GCT GAA ATC GAT TTG CGA                                      394
Asn Ala Cys Ser Ile Ser Ile Asn Gly Asn Ala Pro Ala Glu Ile Asp Leu Arg
            5                   10                  15
```

```
CAA ATG CGA ACT GTC ACT CCC ATT CGT ATG CAA GGA GGC TGT GGT TCA   442
Gln Met Arg Thr Val Thr Pro Ile Arg Met Gln Gly Gly Cys Gly Ser
         20                  25                  30

TGT TGG GCT TTC TCT GGT GTT GCC ACT GAA TCA GCT TAT TTG GCT       490
Cys Trp Ala Phe Ser Gly Val Ala Thr Glu Ser Ala Tyr Leu Ala
 35                  40                  45

CAC CGT AAT CAA TCA TTG GAT CTT GCT GAA CAA TTA GTC GAT TGT       538
His Arg Asn Gln Ser Leu Asp Leu Ala Glu Gln Leu Val Asp Cys
 50                  55                  60                  65

GCT TCC CAA CAC GGT TGT CAT GGT GAT ACC ATT CCA CGT GGT ATT GAA   586
Ala Ser Gln His Gly Cys His Gly Asp Thr Ile Pro Arg Gly Ile Glu
         70                  75                  80

TAC ATC CAA CAT AAT GGT GTC GTC CAA GAA AGC TAC TAT CGA TAC GTT   634
Tyr Ile Gln His Asn Gly Val Val Gln Glu Ser Tyr Tyr Arg Tyr Val
             85                  90                  95

GCA CGA GAA CAA TCA TGC CGA CGA CCA AAT GCA CAA CGT TTC GGT ATC   682
Ala Arg Glu Gln Ser Cys Arg Arg Pro Asn Ala Gln Arg Phe Gly Ile
        100                 105                 110

TCA AAC TAT TGC CAA ATT TAC CCA CCA AAT GCA AAC AAA ATT CGT GAA   730
Ser Asn Tyr Cys Gln Ile Tyr Pro Pro Asn Ala Asn Lys Ile Arg Glu
        115                 120                 125
```

```
GCT TTG GCT CAA ACC CAC AGC GCT ATT ATT GGC ATC AAA    778
Ala Leu Ala Gln Thr His Ser Ala Ile Ile Gly Ile Lys
130                 135                 140         145

GAT TTA GAC GCA TTC CGT CAT TAT GAT GGC CGA ACA ATC ATT CAA CGC    826
Asp Leu Asp Ala Phe Arg His Tyr Asp Gly Arg Thr Ile Ile Gln Arg
                    150                 155                 160

GAT AAT GGT TAC CAA CCA AAC TAT CAC GCT GTC AAC ATT GTT GGT TAC    874
Asp Asn Gly Tyr Gln Pro Asn Tyr His Ala Val Asn Ile Val Gly Tyr
            165                 170                 175

AGT AAC GCA CAA GGT GTC GAT TAT GAT TGG ATC GTA CGA AAC AGT TGG GAT    922
Ser Asn Ala Gln Gly Val Asp Tyr Asp Trp Ile Val Arg Asn Ser Trp Asp
        180                 185                 190

ACC AAT TGG GGT GAT AAT GGT TAC GGT TAT TTT GCT GCC AAC ATC GAT    970
Thr Asn Trp Gly Asp Asn Gly Tyr Gly Tyr Phe Ala Ala Asn Ile Asp
    195                 200                 205

TTG ATG ATG ATT GAA GAA TAT CCA TAT GTT GTC ATT CTC TAAACAAAAA    1019
Leu Met Met Ile Glu Glu Tyr Pro Tyr Val Val Ile Leu
210                 215                 220

GACAATTTCT TATATGATTG TCACTAATTT ATTTAAAATC AAAATTTTTA GAAAATGAAT    1079

AAATTCATTC ACAAAAATTA AAAAAAAAAA AAAAAAAAAA AAAAAAAAAA AAAAAAAAAA    1139

AAAAAAAAAA AAAAAAAAAA AAAAAAAAAA AAA    1172
```

FIG. 2IC

CLONING AND SEQUENCING OF ALLERGENS OF DERMATOPHAGOIDES (HOUSE DUST MITE)

RELATED APPLICATIONS

This application is a continuation-in-part of U.S. Ser. No. 580,655, entitled "Cloning and Sequencing of Allergens of Dermatophagoides (House Dust Mite)", filed Sep. 11, 1990, now abandoned, which is a continuation-in-part of U.S. Ser. No. 458,642, entitled "Cloning of Mite Allergens," filed Feb. 13, 1990, now abandoned. This application also claims priority to an international application, PCT/AU91/00417, filed Sep. 10, 1991. The contents of these applications are incorporated herein by reference.

BACKGROUND

Recent reports have documented the importance of responses to the Group I and Group II allergens in house dust mite allergy. For example, it has been documented that over 60% of patients have at least 50% of their anti-mite antibodies directed towards these proteins (Lind, P. et al., *Allergy*, 39:259–274 (1984); van der Zee, J. S. et al., *J. Allergy Clin. Immunol.*, 81:884–896 (1988)). It is possible that children show a greater degree of reactivity (Thompson, P. J. et al., *Immunology* 64:311–314 (1988)). Allergy to mites of the genus Dermatophagoides (D.) is associated with conditions such as asthma, rhinitis and ectopic dermatitis. Two species, *D. pteronyssinus* and *D. farinae*, predominate and, as a result, considerable effort has been expended in trying to identify the allergens produced by these two species. *D. pteronyssinus* mites are the most common Dermatophagoides species in house dust in Western Europe and Australia. The species *D. farinae* predominates in other countries, such as North America and Japan (Wharton, G. W., *J. Medical Entom*, 12:577–621 (1976)). It has long been recognized that allergy to mites of this genus is associated with diseases such as asthma, rhinitis and atopic dermatitis. It is still not clear what allergens produced by these mites are responsible for the allergic response and associated conditions.

SUMMARY OF THE INVENTION

The present invention relates to isolated DNA which encodes a protein allergen of Dermatophagoides ((D.) house dust mite) or a peptide which includes at least one epitope of a protein allergen of a house dust mite of the genus Dermatophagoides. It particularly relates to DNA encoding major allergens of the species *D. farinae*, designated *Der f* I and *Der f* II, or portions of these major allergens (i.e., peptides which include at least one epitope of *Der f* I or of *Der f* II). It also particularly relates to DNA encoding major allergens of *D. pteronyssinus*, designated *Der p* I and *Der p* II, or portions of these major allergens (i.e., peptides which include at least one epitope of *Der p* I or of *Der p* II).

The present invention further relates to proteins and peptides encoded by the isolated Dermatophagoides (e.g., *D. farinae*, *D. pteronyssinus*) DNA including proteins containing sequence polymorphisms. Several nucleotide and resulting amino acid sequence polymorphisms have been discovered in the *Der p* I, *Der p* II and *Der f* II allergens. All such nucleotide variations and proteins, or portions thereof, containing a sequence polymorphism are within the scope of the invention.

Peptides of the present invention include at least one epitope of a *D. farinae* allergen (e.g., at least one epitope of *Der f* I or *Der f* II) or at least one epitope of a *D. pteronyssinus* allergen (e.g., at least one epitope of *Der p* I or of *Der p* II). It also relates to antibodies specific for *D. farinae* proteins or peptides and to antibodies specific for *D. pteronyssinus* proteins or peptides.

Dermatophagoides DNA, proteins and peptides of the present invention are useful for diagnostic and therapeutic purposes. For example, isolated *D. farinae* proteins or peptides can be used to detect sensitivity in an individual to house dust mites and can be used to treat sensitivity (reduce sensitivity or desensitize) in an individual, to whom therapeutically effective quantities of the *D. farinae* protein or peptide is administered. For example, isolated *D. farinae* protein allergen, such as *Der f* I or *Der f* II, can be administered periodically, using standard techniques, to an individual in order to desensitize the individual. Alternatively, a peptide which includes at least one epitope of *Der f* I or of *Der f* II can be administered for this purpose. Isolated *D. pteronyssinus* protein allergen, such as *Der p* I or *Der p*. II, can be administered as described for *Der f* I or *Der f* II. Similarly, a peptide which includes at least one *Der p* I epitope or at least one *Der p* II epitope can be administered for this purpose. A combination of these proteins or peptides (e.g., *Der f* I and *Der f* II; *Der p* I and *Der p* II; or a mixture of both *Der f* and *Der p* proteins) can also be administered. The use of such isolated proteins or peptides provides a means of desensitizing individuals to important house dust mite allergens.

BRIEF DESCRIPTION OF THE DRAWINGS

FIG. 1 shows the nucleotide and predicted amino acid sequence of cDNA λgt11 pl(13T). Numbers to the right are nucleotide positions whereas numbers above the sequence are amino acid positions. Positive amino acid residue numbers correspond to the sequence of the mature excreted *Der p* I beginning with threonine. Negative sequence numbers refer to the proposed transient pre- and preproenzyme forms of *Der p* I. The arrows indicate the beginning of the proposed proenzyme sequence and the mature *Der p* I, respectively. Residues −15 to −13 enclosed by an open box make up the proposed cleavage for the proenzyme formation, and the dashed residues 52–54 represent a potential N-glycosylation site. The termination TAA codon and the adjacent polyadenylation signal are underlined. Amino acid residues 1–41, 79–95, 111–142, and 162–179 correspond to known tryptic peptide sequences determined by conventional amino acid sequencing analysis.

FIG. 3 is a comparison of N-terminal sequences of *Der p* I and *Der f* I. The amino acid sequence for *Der p* I is equivalent to amino acids 1–20 in FIG. 1; the *Der f* I sequence is from reference (12).

FIG. 4 shows the reactivity of λgt11 pl(13T) with anti-*Der p* I. Lysates from Y1089 lysogens induced for phage were reacted by dot-blot with rabbit anti-*Der p* I (*Der. p* I) or normal rabbit serum (Nrs). Dots (2 μl) were made in triplicate from lysates of bacteria infected with λgt11 pl(13T) (a) or λgt11 (b). When developed with $^{125}$I-protein A and autoradiography only the reaction between λgt11 pl(13T) lysate and the anti-*Der p* I showed reactivity.

FIG. 7 shows the nucleotide and predicted amino acid sequence of cDNA of λgt11 p II (Cl). Numbers to the right are nucleotide positions and numbers above are amino acid positions. Positive numbers for amino acids begin at the known N-terminal of *Der p* II and match the known sequence of the first 40 residues. Residues −1 to −16 resemble a typical leader sequence with a hydrophobic core.

FIG. 8 shows the N-terminal amino acid homology of *Der p* II and *Der f* II. (*Der f* II sequence from reference 30).

FIG. 10 is the nucleotide sequence and the predicted amino acid sequence of cDNA λgt11 f 1. Numbers above are nucleotide positions; numbers to the left are amino acid positions. Positive amino acid residue numbers correspond to the sequence of the mature excreted *Der f* I beginning with threonine. Negative sequence numbers refer to the signal peptide and the proenzyme regions of *Der f* I. The arrows indicate the beginning of the proenzyme sequence and the mature *Der f* I, respectively. The underlined residues −81 to −78 make up the proposed cleavage site for the proenzyme formation, while the underlined residues 53-55 represent a potential N-glycosylation site. The termination TGA codon and the adjacent polyadenylation signal are also underlined. Amino acid residues 1-28 correspond to a known tryptic peptide sequence determined by conventional amino acid sequencing analysis.

FIG. 12 is a comparison of the amino acid sequence in the pre- and pro-peptide regions of *Der f* I with those of rat cathepsin H, rat cathepsin L, papain, aleurain, CP1, CP2, rat cathepsin B, CTLA-2, MCP, *Der p* I and actinidin. Gaps, denoted by dashes, were added for maximal alignment. Double asterisks denote conserved amino acid residues which are shared by greater than 80% of the proenzymes; single asterisks show residues which are conserved in greater than 55% of the sequences. The symbol (.) is used to denote semiconserved equivalent amino acids which are shared by greater than 90% of the proenzyme regions.

FIG. 14 is the nucleotide sequence and the predicted amino acid sequence of *Der f* II cDNA. Numbers to the right are nucleotide positions and numbers above are amino acid residues. The stop (TAA) signal is underlined. The first 8 nucleotides are from the oligonucleotide primer used to generate the cDNA, based on the *Der p* II sequence.

FIG. 16 shows the alignment of *Der f* II and *Der p* II cDNA sequences. Numbers to the right are nucleotide position and numbers above are amino acid residues. The top line gives *Der p* II nucleotide sequence and the second the *Der p* II amino acid residues. The next two lines show differences of *Der f* II to these sequences.

FIG. 18 is a composite alignment of the amino acid sequences of five *Der p* I clones (a)-(e) which illustrates polymorphism in the *Der p* I protein. The numbering refers to the sequence of the *Der p* I(a) clone. The symbol (—) is used to indicate that the amino acid residue of a *Der p* I clone is identical to the corresponding amino acid residue of *Der p* I(a) at that position. The amino acid sequences of these clones indicate that there may be significant variation in *Der p* I, with five polymorphic amino acid residues found in the five sequences.

FIG. 19 is a composite alignment of the amino acid sequences of three *Der p* II clones (c), (1) and (2) which illustrates polymorphism in the *Der p* II protein. The numbering refers to the sequence of the *Der p* II(c) clone. The symbol (.) is used to indicate that the amino acid residue of a *Der p* II clone is identical to the corresponding amino acid residue of *Der p* II (c) at that position.

FIG. 20 is a composite alignment of the amino acid sequences of six *Der f* II clones (i.e., pFL1, pFL2, MT3, MT5, MT18 and MT16) which illustrates polymorphism in the *Der f* II protein. The numbering refers to the sequences of the *Der f* pFL1 clone. The symbol (.) is used to indicate that the amino acid residue of a *Der f* II clone is identical to the corresponding amino acid residue of *Der f* II pFL1 at that position.

FIG. 21 is the nucleotide and predicted amino acid sequences of cDNA λgt11 pI(13T), including the full length of the preproenzyme form of Der p I. Negative sequence numbers refer to the proposed pre- and preproenzyme forms of Der p I.

DETAILED DESCRIPTION OF THE INVENTION

Figure 2:
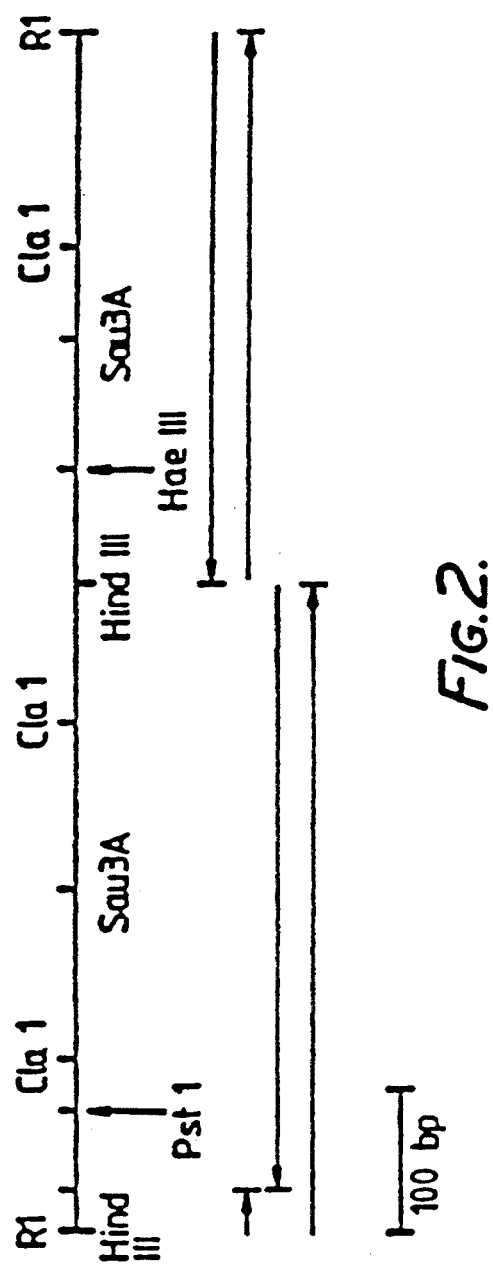
FIG. 2 shows the restriction map of the cDNA insert of clone λgt11 pl(13T) and the strategy of DNA sequencing. Arrows indicate directions in which sequences were read.

The present invention relates to a nucleotide sequence coding for an allergen from the house dust mite Dermatophagoides and to the encoded Dermatophagoides protein or peptide which includes at least one epitope of the Dermatophagoides allergen. It particularly relates to a nucleotide sequence capable of expression in an appropriate host of a major allergen of D. farinae, such as Der f I or Der f II, or of a peptide which includes at least one epitope of Der f I or of Der f II. It also particularly relates to a nucleotide sequence capable of expression in an appropriate host of a major allergen of D. pteronyssinus, such as Der p I or Der p II, or of a peptide which includes at least one epitope of Der p I or of Der p II. The Dermatophagoides nucleotide sequence is useful as a probe for identifying additional nucleotide sequences which hybridize to it and encode other mite allergens, particularly D. farinae or D. pteronyssinus allergens. Further, the present invention relates to nucleotide sequences which hybridize to a D. farinae protein-encoding nucleotide sequence or a D. pteronyssinus protein-encoding nucleotide sequence but which encode a protein from another species or type of house dust mite, such as D. microceras (e.g., Der m I and Der m II).

The encoded Dermatophagoides mite allergen or peptide which includes at least one Dermatophagoides (Der f I or Der f II; Der p I or Der p II) epitope can be used for diagnostic purposes (e.g., as an antigen) and for therapeutic purposes (e.g., to desensitize an individual). Alternatively, the encoded house dust mite allergen can be a protein or peptide, such as a D. microceras protein or peptide, which displays the antigenicity of or is cross-reactive with a Der f or a Der p allergen; generally, these have a high degree of amino acid homology.

Accordingly, the present invention also relates to compositions which include a Dermatophagoides allergen (e.g., Der f I allergen, Der f II allergen; Der p I or Der p II allergen or other D. allergen cross-reactive therewith) or a peptide which includes at least one epitope of a Dermatophagoides allergen (Der f I, Der f II, Der p I, Der p II or other D. allergen cross-reactive therewith) individually or in combination, and which can be used for therapeutic applications (e.g., desensitization). As is described below, DNA coding for major allergens from house dust mites have been isolated and sequenced. In particular, and as is described in greater detail in the Examples, cDNA clones coding for the Der p I, Der p II, Der f I and Der f II allergens have been isolated and sequenced. The nucleotide sequence of each of these clones has been compared with that of the homologous allergen from the related mite species (i.e., Der p I and Der f I; Der p II and Der f II), as has the predicted amino acid sequence of each.

The following is a description of isolation and sequencing of the two cDNA clones coding for Der f allergens and their comparison with the corresponding D. pteronyssinus allergen and a description of use of the nucleotide sequences and encoded products in a diagnostic or a therapeutic context.

Isolation and Sequence Analysis of Der f I

Figure 9:
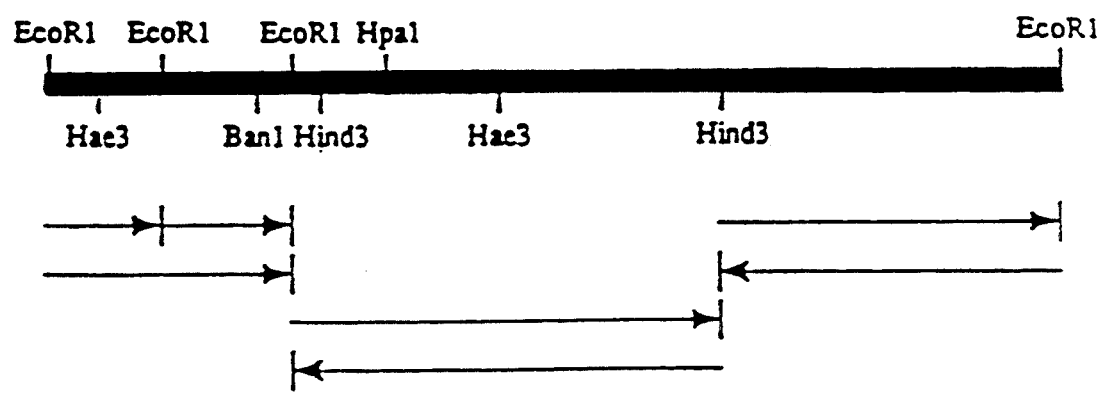
FIG. 9 is a restriction map of the cDNA insert of clone λgt11 f 1, including a schematic representation of the strategy of DNA sequencing. Arrows indicate directions in which sequences were read.
Figure 11:
FIG. 11 is a composite alignment of the amino acid sequences of the mature *Der p* I and *Der f* I proteins. The numbering above the sequence refers to *Der p* I. The asterisk denotes the gap that was introduced for maximal alignment. The symbol (.) is used to indicate that the amino acid residue of *Der f* I at that position is identical to the corresponding amino acid residue of *Der p* I. The arrows indicate those residues making up the active site of *Der p* I and *Der f* I.

A cDNA clone coding for Der f I, a major allergen from the house dust mite D. farinae, has been isolated and sequenced. A restriction map of the cDNA insert of the clone is represented in FIG. 9, as is the strategy of DNA sequencing. This Der f I cDNA clone contains a 1.1-kb cDNA insert encoding a typical signal peptide, a proenzyme region and the mature Der f I protein. The product is 321 amino acid residues; a putative 18 residue signal peptide, an 80 residue proenzyme (pro-peptide) region, and a 223 residue mature enzyme region. The derived molecular weight is 25,191. The nucleotide sequence and the predicted amino acid sequence of the Der f I cDNA are represented in FIG. 10. The deduced amino acid sequence shows significant homology to other cysteine proteases in the pro-region, as well as in the mature protein. Sequence alignment of the mature Der f I protein with the homologous allergen Der p I from the related mite D. pteroyssinus (FIG. 11) revealed a high degree of homology (81%) between the two proteins, as predicted by previous sequencing at the protein level. In particular, the residues comprising the active site of these enzymes were conserved and a potential N-glycosylation site was present at equivalent positions in both mite allergens.

Conserved cysteine residue pairs (31, 71) and (65, 103), where the numbering refers to Der. p I, are apparently involved in disulphide bond formation on the basis of the assumed similarity of the three dimensional structure of Der p I and Der f I to that of papain and actinidin, which also have an additional disulphide bridge. The fifth and final cysteine residue for which there is a homologous cysteine residue in papain and actinidin is the active site cysteine (residue 35 in Der f I). It is not unlikely that the two extra cysteine residues present in Der p I and Der f I may be involved in forming a third disulphide bridge.

The potential N-glycosylation site in Der p I is also present at the equivalent position in Der f I, with conservation of the crucial first and last residues of the tripeptide site. The degree of glycosylation of Der f I and Der p I has yet to be determined. Carbohydrates, including mannose, galactose, N-acetylglucosamine and N-acetylgalactosamine, have been reported in purified preparations of these mite allergens (Chapman, M. D., J. Immunol., 125:587–592 (1980); Wolden, S. et al., Int. Arch. Allergy Appl. Immunol., 68:144–151 (1982)).

Given the degree of homology over the first thirty N-terminal amino acid residues between mature Der p I and Der m I (70%) and mature Der f I and Der m I (97%) with the Der m I residues determined by conventional amino acid sequencing (Platts-Mills TAE et al., In: Mite Allergy, a World-Wide Problem, 27–29 (1988); Lind, P. and N. Horn, In: Mite Allergy, a World-Wide Problem, 30–34 (1988)), it is probable that the full mature Der m I sequence will confirm an overall 70–80% homology between the Group I mite allergens. Der m I is an allergen from D. microceras. High homology between the proenzyme moieties of Der p I and Der f I (91%) over the residues −23 to −1 and the structural analysis of Der f I suggests that the Group I allergens are likely to have N-terminal extension peptides of the mature protein of homologous structure and, at least for the pro-peptide, composition.

Studies on the fine structure of the design of signal sequences have identified three structurally dissimilar regions so far: a positively charged N-terminal (n) region, a central hydrophobic (h) region and a more polar C-terminal (c) region that seems to define the cleavage site (Von Heijne, G., *EMBO J.*, 3:2315-2323 (1984); *Eur. J. Biochem.*, 133:17-21 (1983); *J. Mol. Biol.*, 184:99-105 (1985)). Analysis of the signal peptide of *Der f* I revealed that it, too, contained these regions (FIG. 12). The n-region is extremely variable in length and composition, but its net charge does not vary appreciably with the overall length, and has a mean value of about +1.7. The n-region of the *Der f* I signal peptide, with a length of two residues, has a net charge of +2 contributed by the initiator methionine (which is unformylated and hence positively charged in eukaryotes) and the adjacent lysine (Lys) residue. The h-region of *Der f* I is enriched with hydrophobic residues, the characteristic feature of this region, with only one hydrophilic residue serine (Ser) present which can be tolerated. The overall amino acid composition of the *Der f* I c-region is more polar than that of the h-region as is found in signal sequences with the h/c boundary located between residues −6 and −5, which is its mean position in eukaryotes. Thus, the *Der. f* I pre-peptide sequence appears to fulfill the requirements to which a functional signal sequence must conform.

While the signal sequence of *Der f* I and other cysteine proteases share structural homology, all being composed of the n,h and c-regions, they are highly variable with respect to overall length and amino acid sequence, as is clear in FIG. 12. However, significant sequence homology has been shown between the pro-regions of cysteine protease precursors (Ishidoh, K. et al., *FEBS Letters*, 226:33-37 (1987)). Alignment of the proenzyme regions of *Der f* I and a number of other cysteine proteases (FIG. 12) indicated that these proregions share a number of very conserved residues as well as semi-conserved residues which were present in over half of the sequences. This homology was increased if conservative amino acids such as valine (Val), isoleucine (Ile) and leucine (Leu) (small hydrophobic residues) or arginine (Arg) and Lys (positively charged residues) were regarded as identical. The *Der f* I proregion possessed six out of seven highly conserved amino acids and all the residues at sites of conservative changes. The homology at less conserved sites was lower. Homology in the pro-peptide, in particular the highly conserved residues, may be important when considering the function of the pro-peptide in the processing of these enzymes, since it indicates that these sequences probably have structural and functional similarities.

Highly cross-reactive B cell epitopes on *Der f* I and *Der p* I have been demonstrated using antibodies present in mouse, rabbit and human sera (Heymann, P. W. et al., *J. Immunol.* 137:2841-2847 (1986); Platts-Mills, TAE et al., *J. Allergy Clin. Immunol.* 78:398-407 (1986)). However, species-specific epitopes have also been defined in these systems. Murine monoclonal antibodies bound predominantly to species-specific determinants (Platts-Mills TAE et al., *J. Allergy Clin Immunol.* 139:1479-1484 (1987)). Some 40% of rabbit anti-*Der p* I reactivity was accounted for by epitopes unique to *Der p* I (Platts-Mills, TAE et al., *J. Allergy Clin. Immunol.* 78:398-407 (1986)), and some species-specific binding of antibodies from allergic humans was observed, although the majority bind to cross-reactive epitopes (Platts-Mills TAE et al., *J. Immunol.* 139:1479-1484 (1987)).

Figure 13A:
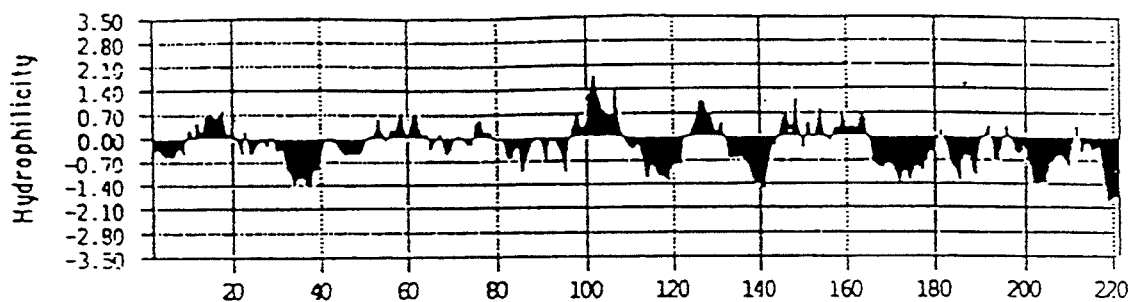
FIG. 13 is a hydrophilicity plot of the *Der p* I mature protein and a hydrophilicity plot of the *Der f* I mature protein produced using the Hopp-Woods algorithm computed with the Mac Vector Sequence Analysis Software (IBI, New Haven) using a 6 residue window. Positive values indicate relative hydrophilicity and negative values indicating relative hydrophobicity.
Figure 13B:
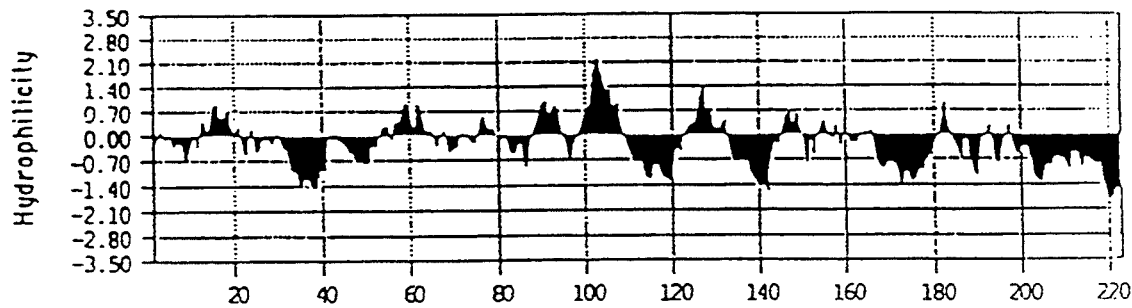

The recombinant DNA strategy of gene fragmentation and expression was used (Greene, W. K. et al.,

*Immunol.* (1990)) to define five antigenic regions of recombinant *Der p* I which contained B cell epitopes recognized by a rabbit anti-*Der p* I antiserum. Using the technique of immunoabsorption, three of these putative epitopes were shown to be shared with *Der f* I (located on regions containing amino acid residues 34–47, 60–72 and 166–194) while two appeared to be specific for *Der p* I (regions 82–99 and 112–140). Differences in the reactivity of these peptides to rabbit anti-*D. farinae* supported the above division into cross-reactive and species-specific epitopes. The sequence differences shown between the *Der p* I and the *Der f* I proteins are primarily located in the N and C terminal regions, as well as in an extended surface loop (residues 85–136) linking the two domains of the enzyme that includes helix D (residues 127–136), as predicted from the secondary and tertiary structures of papain and actinidin (Baker, E. N. and J. Drenth, In: *Biological Macromolecules and Assemblies*, Vol. 3, pp. 314–368, John Wiley and Sons, NY (1987)). The surface location of these residues is supported by the hydrophilicity plots of *Der p* I and *Der f* I in FIG. 13, which illustrate the predominantly hydrophilic nature of this region that predicts surface exposure. This region also contains the two species-specific B cell epitopes recognized by the rabbit anti-*Der p* I serum (see above). Analysis of the sequences in the regions containing the cross-reactive epitopes (located in regions 34–47 and 60–72) are completely conserved between *Der p* I and *Der f* I, while the majority of residues in a third cross-reactive epitope-containing region (residues region 166–194) were conserved.

Expression of cDNA encoding *Der f* I results in production of pre-pro-*Der f* I protein in *E. coli*, a recombinant protein of greater solubility, stability and antigenicity than that of recombinant *Der p* I. Protein encoded by *Der f* I cDNA has been expressed using a pGEX vector and has been shown by radioimmune assay to react with rabbit anti-*D. farinae* antibodies. The availability of high yields of soluble *Der f* I allergen and antigenic derivatives will facilitate the development of diagnostic and therapeutic agents and the mapping of B and T cell antigenic determinants.

With the availability of the complete amino acid sequence of recombinant *Der f* I, mapping of the epitopes recognized by both the B and T cell compartments of the immune system can be carried out. The use of techniques such as the screening of overlapping synthetic peptides, the use of monoclonal antibodies and gene fragmentation and expression should enable the identification of both the continuous and topographical epitopes of *Der f* I. It will be particularly useful to determine whether allergenic (IgE-binding) determinants have common features and are intrinsically different from antigenic (IgG-binding) determinants and whether T cells recognize unique epitopes different from those recognized by B cells. Studies to identify the *Der f* I epitopes reactive with mite allergic human IgE antibodies and the division of these into determinants cross-reactive with *Der p* I and determinants unique to *Der f* I can also be carried out. B cell (and T cell) epitopes specific for either species can be used to provide useful diagnostic reagents for determining reactivity to the different mite species, while cross-reacting epitopes are candidates for a common immunotherapeutic agent.

As described in detail in the Examples, a cDNA clone coding for *Der p* I which contained a 0.8-kb cDNA insert has been isolated. Sequence analysis revealed that the 222 amino acid residue mature recombinant *Der p* I protein showed significant homology with a group of cysteine proteases, including actinidin, papain, cathepsin H and cathepsin B.

Isolation and Sequence Analysis of Der f II

Figure 15:
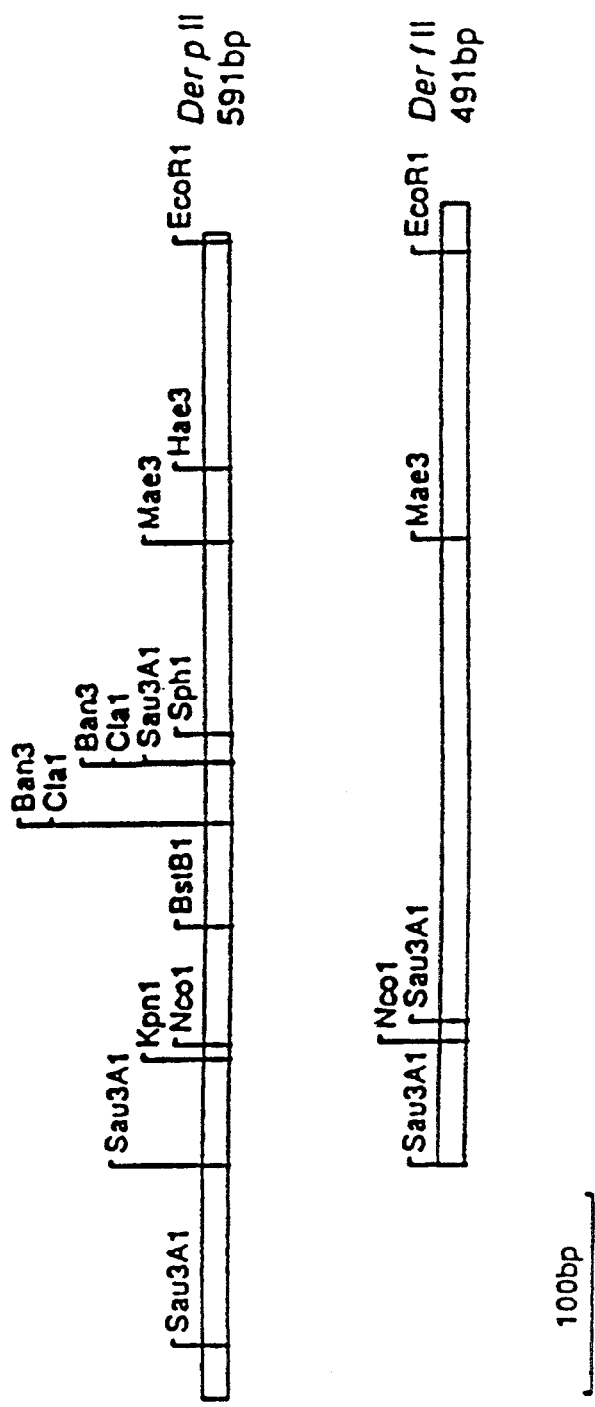
FIG. 15 is a restriction map of *Der f* II cDNA, which was generated by computer from the sequence data. A map of *Der p* II similarly generated is shown for comparison. There are few common restriction enzyme sites conserved. Sites marked with an asterisk were introduced by cloning procedures.

A cDNA clone coding for Der f II, a major allergen from the house dust mite D. farinae, has been isolated and sequenced, as described in the Examples. The nucleotide sequence and the predicted amino acid sequence of the Der f II cDNA are represented in FIG. 14. A restriction map of the cDNA insert of a clone coding for Der f II is represented in FIG. 15.

FIG. 16 shows the alignment of Der f II and Der p II cDNA sequences. The homology of the sequence of Der f II with Der p II (88%) is higher than the 81% homology found with Der p I and Der f I, which is significantly different ($p < 0.05$) using the chi$^2$ distribution. The reason for this may simply be that the Group I allergens are larger and each residue may be less critical for the structure and function of the molecule. It is known, for example, that assuming they adopt a similar conformation to other cysteine proteases, many of the amino acid differences in Der p I and Der f I lie in residues linking the two domain structures of the molecules. The 6 cysteine molecules are conserved between the group II allergens, suggesting a similar disulphide bonding, although this may be expected, given the high overall homology. Another indication of the conservation of these proteins is that 34/55 of the nucleotide changes of the coding sequence are in the third base of a codon, which usually does not change the amino acid. Residues that may be of importance in the function of the molecule are Ser 57 where all three bases are changed but the amino acid is conserved. A similar phenomenon exists at residue 88, where a complete codon change has conserved a small aliphatic residue. Again, like Der p II, the Der f II cDNA clone does not have a poly A tail, although the 3' non-coding region is rich in adenosine and has two possible polyadenylation signals ATAA. The nucleotides encoding the first four residues are from the PCR primer which was designed from the known homology of Der p II and Der f II from N-terminal amino acid sequencing. A primer based on the C-terminal sequence can now be used to determine these bases, as well as the signal sequence.

Uses of the Subject Allergenic Proteins/Peptides and DNA Encoding Same

The materials resulting from the work described herein, as well as compositions containing these materials, can be used in methods of diagnosing, treating and preventing allergic responses to mite allergens, particularly to mites of the genus Dermatophagoides, such as D. farinae and D. pteronyssinus. In addition, the cDNA (or the mRNA from which it was transcribed) can be used to identify other similar sequences. This can be carried out, for example, under conditions of low stringency and those sequences having sufficient homology (generally greater than 40%) can be selected for further assessment using the method described herein. Alternatively, high stringency conditions can be used. In this manner, DNA of the present invention can be used to identify sequences coding for mite allergens having amino acid sequences similar to that of Der f I, Der f II, Der p I or Der p II. Thus, the present invention includes not only D. farinae and D. pteronyssinus allergens, but other mite allergens as well (e.g., other mite allergens encoded by DNA which hybridizes to DNA of the present invention).

Proteins or peptides encoded by the cDNA of the present invention can be used, for example, as "purified" allergens. Such purified allergens are useful in the standardization of allergen extracts or preparations which can be used as reagents for the diagnosis and treatment of allergy to house dust mites. Through use of the peptides of the present invention, allergen preparations of consistent, well-defined composition and biological activity can be made and administered for therapeutic purposes (e.g., to modify the allergic response of a house dust mite-sensitive individual). Der f I or Der f II peptides or proteins (or modified versions thereof, such as are described below) may, for example, modify B-cell response to Der f I or Der f II, T-cell response to Der f I and Der f II, or both responses. Similarly, Der p I or Der p II proteins or peptides may be used to modify B-cell and/or T-cell response to Der p I or Der p II. Purified allergens can also be used to study the mechanism of immunotherapy of allergy to house dust mites, particularly to Der f I, Der f II, Der p I and Der p II, and to design modified derivatives or analogues which are more useful in immunotherapy than are the unmodified ("naturally-occurring") peptides.

In those instances in which there are epitopes which are cross-reactive, such as the three epitopes described herein which are shared by Der f I and Der p I, the area(s) of the molecule which contain the cross-reactive epitopes can be used as common immunotherapeutic peptides to be administered in treating allergy to the two (or more) mite species which share the epitope. For example, the cross-reactive epitopes could be used to induce IgG blocking antibody against both allergens (e.g., Der f I and Der p I allergen). A peptide containing a univalent antibody epitope can be used, rather than the entire molecule, and may prove advantageous because the univalent antibody epitope cannot crosslink mast cells and cause adverse reactions during desensitizing treatments. It is also possible to attach a B cell epitope to a carrier molecule to direct T cell control of allergic responses.

Alternatively, it may be desirable or necessary to have peptides which are specific to a selected Dermatophagoides allergen. As described herein, two epitopes which are apparently Der p I-specific have been identified. A similar approach can be used to identify other species-specific epitopes (e.g., Der p I or II, Der f I or II). The presence in an individual of antibodies to the species-specific epitopes can be used as a quick serological test to determine which mite species is causing the allergic response. This would make it possible to specifically target therapy provided to an individual to the causative species and, thus, enhance the therapeutic effect.

Work by others has shown that high doses of allergens generally produce the best results (i.e., best symptom relief). However, many people are unable to tolerate large doses of allergens because of allergic reactions to the allergens. Modification of naturally-occurring allergens can be designed in such a manner that modified peptides or modified allergens which have the same or enhanced therapeutic properties as the corresponding naturally-occurring allergen but have reduced side effects (especially anaphylactic reactions) can be produced. These can be, for example, a peptide of the present invention (e.g., one having all or a portion of the amino acid sequence of Der f I or Der f II, Der p I or Der p II). Alternatively, a combination of peptides can be administered. A modified peptide or peptide analogue (e.g., a peptide in which the amino acid sequence has been altered to modify immunogenicity and/or reduce allergenicity or to which a component has been added for the same purpose) can be used for desensitization therapy.

Administration of the peptides of the present invention to an individual to be desensitized can be carried out using known techniques. A peptide or combination of different peptides can be administered to an individual in a composition which includes, for example, an appropriate buffer, a carrier and/or an adjuvant. Such compositions will generally be administered by injection, inhalation, transdermal application or rectal administration. Using the information now available, it is possible to design a Der p I, Der p II, Der f I or Der f II peptide which, when administered to a sensitive individual in sufficient quantities, will modify the individual's allergic response to Der p I, Der f II, Der f I and/or Der f II. This can be done, for example, by examining the structures of these allergens, producing peptides to be examined for their ability to influence B-cell and/or T-cell responses in house dust mite-sensitive individuals and selecting appropriate epitopes recognized by the cells. Synthetic amino acid sequences which mimic those of the epitopes and which are capable of down regulating allergic response to Der p I, Der p II, Der f I or Der f II allergens can be made. Proteins, peptides or antibodies of the present invention can also be used, in known methods, for detecting and diagnosing allergic response to Der f I or Der f II. For example, this can be done by combining blood obtained from an individual to be assessed for sensitivity to one of these allergens with an isolated allergenic peptide of house dust mite, under conditions appropriate for binding of or stimulating components (e.g., antibodies, T cells, B cells) in the blood with the peptide and determining the extent to which such binding occurs. Der f and Der p proteins or peptides can be administered together to treat an individual sensitive to both allergen types.

It is now also possible to design an agent or a drug capable of blocking or inhibiting the ability of Der p I, Der p II, Der f I or Der f II to induce an allergic reaction in house dust mite-sensitive individuals. Such agents could be designed, for example, in such a manner that they would bind to relevant anti-Der p I, anti-Der p II, anti-Der f I or anti-Der f II IgEs, thus preventing IgE-allergen binding and subsequent mast cell degranulation. Alternatively, such agents could bind to cellular components of the immune system, resulting in suppression or desensitization of the allergic response to these allergens. A non-restrictive example of this is the use of appropriate B- and T-cell epitope peptides, or modifications thereof, based on the cDNA/protein structures of the present invention to suppress the allergic response to these allergens. This can be carried out by defining the structures of B- and T-cell epitope peptides which affect B- and T-cell function in in vitro studies with blood cells from house dust mite-sensitive individuals.

The cDNA encoding Der p I, Der p II, Der f I or Der f II or a peptide including at least one epitope thereof can be used to produce additional peptides, using known techniques such as gene cloning. A method of producing a protein or a peptide of the present invention can include, for example, culturing a host cell containing an expression vector which, in turn, contains DNA encoding all or a portion of a selected allergenic protein or peptide (e.g., Der p I, Der p II, Der f I, Der f II or a peptide including at least one epitope). Cells are cultured under conditions appropriate for expression of the DNA insert (production of the encoded protein or peptide). The expressed product is then recovered, using known techniques. Alternatively, the allergen or portion thereof can be synthesized using known mechanical or chemical techniques. As used herein, the term protein or peptide refers to proteins or peptides made by any of these techniques. The resulting peptide can, in turn, be used as described previously.

DNA to be used in any embodiment of this invention can be cDNA obtained as described herein or, alternatively, can be any oligodeoxynucleotide sequence having all or a portion of the sequence represented in FIGS. 1, 7, 10 and 14 or their functional equivalent. Such oligodeoxynucleotide sequences can be produced chemically or mechanically, using known techniques. A functional equivalent of an oligonucleotide sequence is one which is capable of hybridizing to a complementary oligonucleotide sequence to which the sequence (or corresponding sequence portions) of FIGS. 1, 7, 10 and 14 hybridizes and/or which encodes a product (e.g., a polypeptide or peptide) having the same functional characteristics of the product encoded by the sequence (or corresponding sequence portion) represented in these figures. Whether a functional equivalent must meet one or both criteria will depend on its use (e.g., if it is to be used only as an oligoprobe, it need meet only the first criterion and if it is to be used to produce house dust mite allergen, it need only meet the second criterion).

The structural information now available (e.g., DNA, protein/peptide sequences) can also be used to identify or define T cell epitope peptides and/or B cell epitope peptides which are of importance in allergic reactions to house dust mite allergens and to elucidate the mediators or mechanisms (e.g., interleukin-2, interleukin-4, gamma interferon) by which these reactions occur. This knowledge should make it possible to design peptide-based house dust mite therapeutic agents or drugs which can be used to modulate these responses.

The present invention will now be further illustrated by the following Examples, which are not intended to be limiting in any way.

EXAMPLE 1

MATERIALS AND METHODS

Cloning and Expression of Der p I cDNA

Polyadenylated mRNA was isolated from the mite *Dermatophagoides pteronyssinus* cultured by Commonwealth Serum Laboratories, Parkville, Australia, and cDNA was synthesized by the RNA-ase H method (5) using a kit (Amersham, International, Bucks). After the addition of EcoRI linkers the cDNA was ligated into λgt11 and plated in *E. coli* Y1090 (r-) (Promega Biotec, Madison, Wis.), to produce a library of $5 \times 10^5$ recombinants. Screening was performed by plaque radioimmune assay (6) using a rabbit anti-Der p I antiserum (7). Reactivity was detected by hydrochloride in 0.1M sodium acetate buffer pH 5.2 were then added and the mixture was homogenized and spun at 10,000 rpm for 30 min in a Sorval SS34 rotor. The supernatant was collected and layered onto a CsCl pad (5 ml of 4.8M CsCl in 10 mM EDTA) and centrifuged at 37,000 rpm for 16 h at 15° C. in a SW41 TI rotor (Beckman Instruments, Inc., Fullerton, Calif.). The DNA band at the interphase was collected and diluted 1:15 in 10 mM Tris HCl/1 mM EDTA buffer, pH 8.0. Banding of genomic DNA in CsCl was carried out by the standard method.

Isolation of DNA from λgt11 p1 cDNA Clone

Phage DNA from λgt11 p1 clone was prepared by a rapid isolation procedure. Clarified phage plate lysate (1 ml) was mixed with 270 μl of 25% wt/vol polyethylene glycol (PEG 6000) in 2.5M NaCl and incubated at room temperature for 15 min. The mixture was then spun for 10 5 min in a microfuge (Eppendorf, Federal Republic of Germany), and the supernatant was removed. The pellet was dissolved in 100 μl of 10 mM Tris/HCl pH 8.0 containing 1 mM EDTA and 100 mM NaCl. This DNA preparation was extracted 3 times with phenol/-chloroform (1:1) and the DNA was precipitated by ethanol.

DNA Hybridization

Nucleic acid was radiolabelled with $^{32}P$ by nick translation (10). DNA samples were digested with appropriate restriction enzymes using conditions recommended by the supplier. Southern blots were prepared using Zeta-Probe membranes (Bio-Rad Laboratories, Richmond, Calif.). Prehybridization, hybridization, posthybridization washes were carried out according to the manufacturers recommendations (bulletin 1234, Bio-Rad Laboratories).

Cloning and DNA Sequencing

To clone the 0.8-kb cDNA insert from clone λgt11 p1 into plasmid pUC8, phage DNA was digested with EcoRI restriction enzyme and then ligated to EcoRI-digested pUC8 DNA and used to transform *Escherichia coli* JM83. The resulting recombinant plasmid was designated as pHDM 1.

To obtain clones for DNA sequence analysis, the cDNA insert was isolated from pHDM 1 and ligated to M13-derived sequencing vectors mp18 and mp19 (16). Transformation was carried out using *E. coli* JM107 and sequencing was performed by the dideoxynucleotide chain termination method (11).

RESULTS

Several phage clones reacted with the rabbit anti *Der p* I serum and hybridized with all 3 oligonucleotide probes. One of these, λgt11 p1(13T), was examined further. The nucleotide sequence of the cDNA insert from this clone, λgt11 p1, was determined using the sequencing strategy shown in FIG. 2. The complete sequence was shown to be 857 bases long and included a 69-base-long 5' proximal end sequence, a coding region for the entire native *Der p* I protein of 222 amino acids with a derived molecular weight of 25,371, an 89-base-long 3' noncoding region and a poly (A) tail of 33 residues (FIG. 1).

The assignment of a threonine residue at position 1 as the NH$_2$-terminal amino acid of *Der p* I was based on data obtained by NH$_2$-terminal amino acid sequencing of the pure protein isolated from mite excretions (17). The predicted amino acid sequence matched with data obtained by amino acid sequence analysis of the NH$_2$-terminal region as well as with internal sequences derived from analyses of tryptic peptides (FIG. 1). The complete mature protein is coded by a single open reading frame terminating at the TAA stop codon at nucleotide position 736–738. At present, it is not certain whether the first ATG codon at nucleotide position 16–18 is the translation initiation site, since the immediate flanking sequence of this ATG codon (TTGATGA) showed no homology with the Kozak consenses sequence (ACCATGG) for the eukaryotic translation initiation sites (18). In addition, the 5' proximal end sequence does not code for a typical signal peptide sequence (see below).

The amino acid sequence predicted by nucleotide analysis is shown in FIG. 1. A protein data-base search revealed that the *Der p* I amino acid sequence showed homology with a group of cysteine proteases. Previous cDNA studies have shown that lysosomal cathepsins B, a mouse macrophage protease and a cysteine protease from an amoeba have transient pre- and proform intermediates (19–21), and inspection of the amino acid sequence at the 5' proximal end of the λgt11 p1 cDNA clone suggests that *Der p* I may be similar. First, the hydrophilicity plot (22) of the sequence preceding the mature protein sequence lacks the characteristic hydrophobic region of a signal peptide (23) and second, an Ala-X-Ala sequence, the most frequent sequence preceding the signal peptidase cleavage site (24,25), is present at positions −13, −14, −15 (FIG. 1). Therefore, it is proposed that cleavage between pro-*Der p* I sequence and the pre-*Der p* I sequence occurs between Ala (−13) and Phe (−12). Thus, pro-*Der p* I sequence begins at residues Phe (−12) and ends at residues Glu (−1). The amino acids residues numbered −13 to −23 would then correspond to a partial signal peptide sequence. The full length of the *Der p* I preproenzyme sequence has been determined and is shown in FIG. 21. The negative sequence numbers refer to the pre- and preproenzyme forms of *Der p* I.

When the 857-bp cDNA insert was radiolabelled and hybridized against a Southern blot of EcoRI-digested genomic DNA from house dust mite, hybridization to bands of 1.5, 0.5, and 0.35 kb was observed (data not shown). As shown in the restriction enzyme map of the cDNA insert (FIG. 2), there was no internal EcoRI site and the multiple hybridization bands observed suggest that *Der p* I is coded by a noncontiguous gene. The results also showed little evidence of gene duplication since hybridization was restricted to fragments with a total length of 2.4 kb.

The N-terminal can be compared with N-terminal of the equivalent protein from *D.farinae* (*Der f* I) (12). There is identity in 11/20 positions of the sequences available for comparison (FIG. 3).

To examine the protein produced by λgt11 p1(13T), phage was lysogenized in Y1089 (r-) and the bacteria grown in broth culture at 30° C. Phage was induced by temperature switch and isopropyl thiogalactopyranoside (IPTG) (6) and the bacteria were suspended in PBS to 1/20 of the culture volume, and sonicated for an antigen preparation. When examined by 7.5% SDS-PAGE electrophoresis it was found that λgt11 p1(13T) did not produce a Mr 116K β-galactosidase band but instead produced a 140K band consistent with a fusion protein with the *Der p* I contributing a 24 kDa moiety (6). Rabbit anti *Der p* I was shown to react with the lysate from λgt11 p1(13T) (FIG. 4).

EXAMPLE 2

Expression of *Der p* I cDNA Products Reactive with IgE from Allergic Serum

Figure 5:
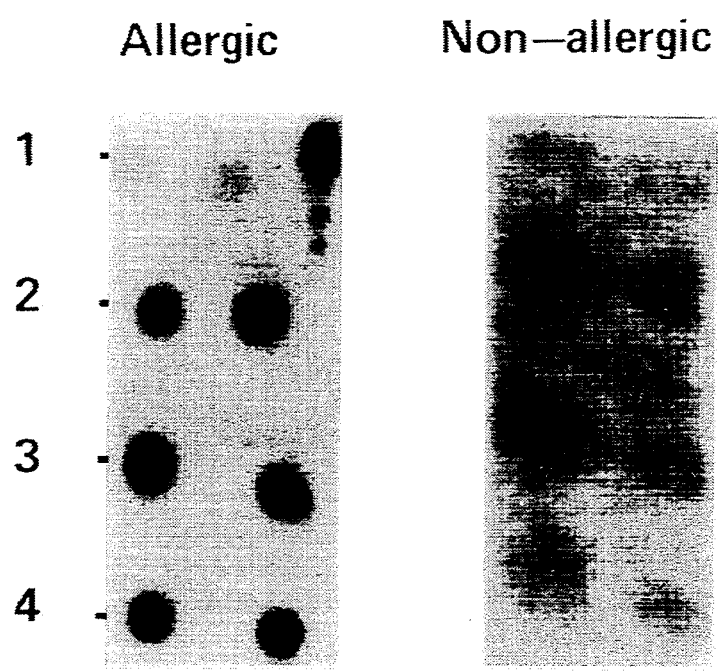
FIG. 5 shows reaction of clone pGEX-pl(13T) with IgE in allergic serum. Overnight cultures of pGEX or pGEX-pl where diluted 1/10 in broth and grown for 2 hours at 37° C. They were induced with IPTG, grown for 2 hours at 37° C. The bacteria were pelletted and resuspended in PBS to 1/10 the volume of culture media. The bacteria were lysed by freeze/thaw and sonication. A radioimmune dot-blot was performed with 2 μl of these lysates using mite-allergic or non-allergic serum. The dots in row 1 were from *E. coli* containing pGEX and row 2-4 from different cultures of *E. coli* infected with pGEX-pl(13T). Reactivity to pGEX-pl(13T) was found with IgE in allergic but not non-allergic serum. No reactivity to the vector control or with non-allergic serum was found.

The DNA insert from λgt11 p1(13T) which codes for *Der p* I was subcloned into the EcoRI site of the plasmid expression vector (pGEX)(26) where it could be expressed as a fusion with a glutathione transferase molecule. *E. coli* infected with this plasmid pGEX-pl(13T) or with the vector alone were grown to a log phase culture and harvested by centrifugation. The bacteria were suspended in PBS to 1/20 of their culture volume and lysed by freeze-thawing. The lysate was shown by sodium dodecylsulphate polyacrylamide electrophoresis to express a fusion protein in high concentration of the expected Mr 50,000. These lysates were then tested for their ability to react with IgE from allergic serum by radioimmune dot-blot conducted by the method described by Thomas and Rossi (27). The serum was taken from donors known to be mite-allergic or from nonallergic controls. Reactivity was developed by $^{125}$I-monoclonal anti-IgE and autoradiography. FIG. 5 shows the lysate from pGEX-pl(13T), but not the vector control reacted with IgE in allergic serum, but not non allergic serum.

EXAMPLE 3

Inhibition of IgE Antibody Responses to *Der p* I by Treatment with the Product from a CDNA Clone Coding for *Der p* I

*E. coli* lysogenized by λgt11 pl(13T) were grown and induced by temperature switch to produce a recombinant fusion protein which was consistent with a 24 kD *Der p* I moiety and a 116 kD β-galactosidase moiety (pl(13T) (28). This protein was mostly insoluble and could be isolated to about 90% purity, judged by sodium didodecyl polyacrylamide electrophoresis, by differential centrifugation. A similar protein was produced from another gt11 cDNA mite clone λgt pX (2c). To test for the ability of the recombinant protein to modify IgE antibody responses to *Der p* I, groups of 4–5 CBA mice were injected intraperitoneally with 2 mg of the pl(13T) or pX (2c) fusion proteins and after 2 days given a subcutaneous injection of 5 μg of native *Der p* I (from mite culture medium) in aluminium hydroxide gel. The IgE antibody titres were measured by passive cutaneous anaphylaxis (PCA) after 3 and 6 weeks. The methods and background data for these responses have been described by Stewart and Holt (29). For a specificity control, groups of mice injected with pl(13T) or pX (2c) were also injected with 10 μg of ovalbumin in alum. Responses were compared to mice without prior pl(13T) or pX (2c) treatment (Table 1). After 3 weeks mice either not given an injection of recombinant protein or injected with the control pX (2c) had detectable anti *Der p* I PCA titres (½ or greater). Only 1/5 of mice treated with recombinant pl(13T) had a detectable titre and this at ¼ was lower than all of the titres of both control groups. Titres of all groups at 6 weeks were low or absent (not shown). The PCA response to ovalbumin was not significantly affected by treatment with recombinant proteins. These data show the potential of the recombinant proteins to specifically decrease IgE responses as required for a desensitizing agent.

TABLE 1

| | Inhibition of anti-Der p I IgE by preinjection with with recombinant Der p I. | | | |
|---|---|---|---|---|
| group | preinjection −2 days | immunizing injection (d0) (5 μg/alum) | IgE (PCA) titres at d21 responders | titres |
| 1 | — | Der p I | 4/4 | 1/16–1/64 |
| 2 | pX(2C) | Der p I | 5/5 | 1/8–1/16 |
| 3 | pl(13T) | Der p I | 1/5* | 1/4* |

TABLE 1-continued

| | Inhibition of anti-Der p I IgE by preinjection with with recombinant Der p I. | | | |
|---|---|---|---|---|
| group | preinjection −2 days | immunizing injection (d0) (5 μg/alum) | IgE (PCA) titres at d21 responders | titres |
| 4 | — | ovalbumin | 4/4 | 1/64–1/256 |
| 5 | pX(2C) | ovalbumin | 5/5 | 1/32–1/128 |
| 6 | pl(13T) | ovalbumin | 5/5 | 1/64–1/256 |

*Mann Whitney analysis.

Mice were given a preinjection on day −2 and then immunized with *Der p* I or ovalbumin on day 0. Serum antibody titres were measured on day 21 and 42 by PCA in rat skin. Significant anti-*Der p* I titres were not detected on day 42 (not shown). The PCA were measured to *Der p* I for groups 1–3 and ovalbumin for groups 4–6. The anti-*Der p* I titres were lower (p<0.001)* when pretreated with recombinant *Der p* I pl(13T).
*Mann Whitney analysis.

EXAMPLE 4

Expression of *Der p* I Antigenic Determinants by Fragments of the cDNA from λgt11 pl(13T)

The cDNA from λgt11 (13T) coding for *Der p* I was fragmented by sonication. The fragments (in varying size ranges) were isolated by electrophoresis, filled in by the Klenow reaction to create blunt ends. EcoRI linkers were attached and the fragment libraries cloned in λgt11. The methods used for the fragments cloning were the same as that used for cDNA cloning (6). Plaque immunoassay was used for screening with rabbit anti-*Der p* I. Three phage clones reacting with the antiserum were isolated and the oligonucleotide sequences of the cloned fragments obtained. Two of these were found to code for *Der p* I amino acids 17–55 (see FIG. 1 for numbering) and one for amino acids 70–100. Such fragments will eventually be useful for both diagnostic reagents to determine epitope reactivity and for therapy where molecules of limited allergenicity may increase safety of desensitisation.

EXAMPLE 5

Cloning and Expression of cDNA Coding for the Major Mite Allergen *Der p* II

Figure 6:
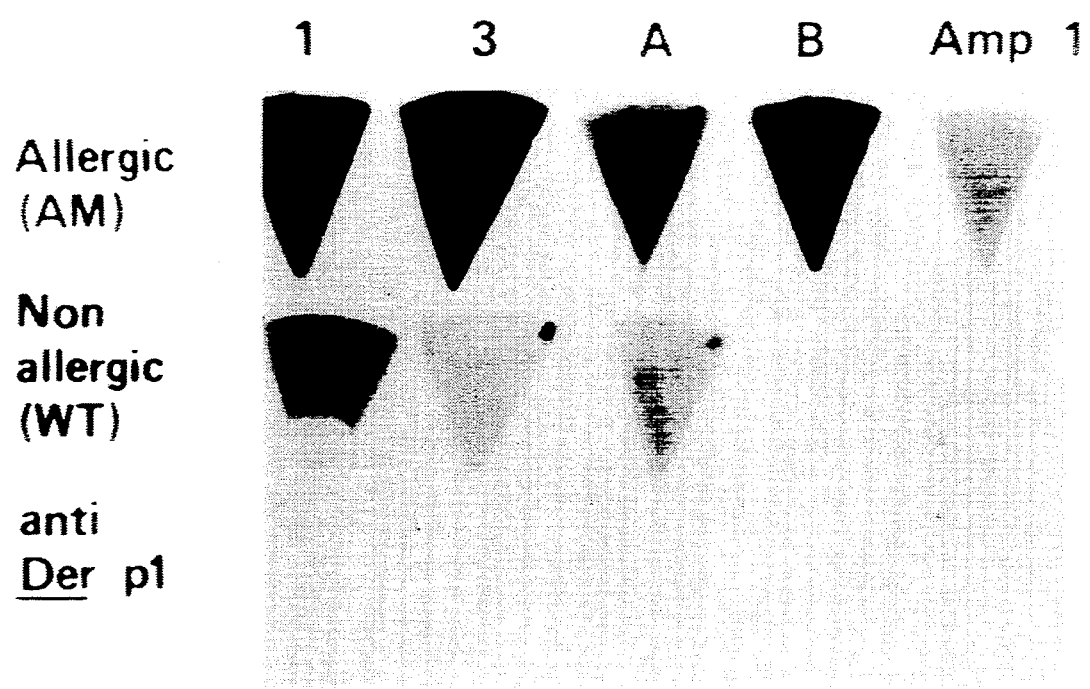
FIG. 6 shows seroreactivity of cDNA clones coding for *Der p* II in plaque radioimmune assay. Segments of nitrocellulose filters from plaque lifts were taken from clones 1, 3, A, B and the vector control Ampl. These were reached by immunoassay for human IgE against allergic serum (AM) in row 1, non-allergic serum (WT) in row 2 and by protein A immunoassay for *Der p* I with rabbit antiserum in row 3. The clones 1, 3 and B reacted strongly with allergic serum but not non-allergic or vector control. (Clone B and vector control were not tested with non-allergic serum).

The *Dermatophagoides pteronyssinus* cDNA library in λgt11 previously described was screened by plaque radioimmune assay using nitrocellulose lifts (6). Instead of using specific antisera the sera used was from a person allergic to house dust mites. The serum (at ½ dilution) was absorbed with *E. coli*. To detect reactivity an $^{125}$I labelled monoclonal anti-IgE was used (at 30 ng/ml with 2×10$^6$ cpm/ml (approx. 30% counting efficiency)). After 1 hour the filters were washed and autoradiography performed. Using this procedure 4 clones reacting with human IgE were isolated. It was found they were related by DNA hybridization and had an identical pattern of reactivity against a panel of allergic sera. FIG. 6 shows IgE reactivity in plaque radioimmunoassay against allergic serum (AM) (top row) or non allergic (WT). Here, clones 1, 3 and 8 react strongly, but only against allergic sera. The amp 1 segments (present in row 1) are a λgt11 vector control. The bottom row is an immunoassay with rabbit anti-*Der p* I, developed by $^{125}$I staphylococcus protein A which shows no significant reactivity. The clones were tested against a panel of sera. Serum from five patients without allergy to mite did not react, but serum from 14/17 people with mite allergy showed reactivity. The DNA insert from the clone λgt11 pII(C1) was subcloned into M13 mp18 and M13 mp19 and sequenced by the chain termination method. The nucleotide sequence (FIG. 7) showed this allergen was *Der p* II by (a) the homology of the inferred amino acid sequence of residues 1–40 with that of the N-terminal amino acid of *Der p* II (30); and (b) the homology of this sequence with the equivalent *Der f* II allergen from *Dermatophagoides farinae* (30).

EXAMPLE 6

Isolation and Characterization of cDNA Coding for *Der f* I

MATERIALS AND METHODS

*Dermatophagoides farinae* Culture

Mites were purchased from Commonwealth Serum Laboratories, Parkville, Australia.

Construction of the *D. farinae* cDNA λgt11 Library

Polyadenylated mRNA was isolated from live *D. farinae* mites and cDNA was synthesized by the RNase H method (Gubler, V. and B. J. Hoffman, *Gene* 25:263–269 (1983)) using a kit (Amersham International, Bucks.). After the addition of EcoRI linkers (New England Biolabs, Beverly, Mass.) the cDNA was ligated to alkaline phosphatase treated λgt11 arms (Promega, Madison, Wis.). The ligated DNA was packaged and plated in *E. coli* Y1090 (r-) to produce a library of $2 \times 10^4$ recombinants.

Isolation of *Der f* I cDNA Clones from the *D. farinae* cDNA λgt11 Library

Screening of the library was performed by hybridization with two probes comprising the two *Der p* I cDNA BamHI fragments 1–348 and 349–857 generated by BamHI digestion of a derivative of the *Der p* I cDNA which has had two BamHI restriction sites inserted between amino acid residues −1 and 1 and between residues 116 and 117 by site-directed mutagenesis (Chua, K. Y. et al., *J. Exp. Med.* 167:175–182 (1988)). The probes were radiolabelled with $^{32}p$ by nick translation. Phage were plated at 20,000 pfu per 150 mm petri dish and plaques were lifted onto nitrocellulose (Schleicher and Schull, Dassel, FRG), denatured and baked (Maniatis, T. et al., *Molecular Cloning: A Laboratory Manual,* Cold Spring Harbor Laboratory Press (1982)). Prehybridizations were performed for 2 hours at 42° C. in 50% formamide/5×SSCE/1×Denhardt's/poly C (0.1 mg/ml)/poly U(0.1 mg/ml) with hybridization overnight at 42° C. at $10^6$ cpm/ml. Post hybridization washes consisted of 15 min washes at room temperature with 2×sodium chloride citrate (SSC)/0.1% sodium dodecylsulphate (SDS), 0.5×SSC/0.1% SDS, 0.1×SSC/0.1% SDS successively and a final wash at 50° C. for 30 min in 0.1×SSC/1% SDS.

Isolation of DNA from λgt11 f 1 cDNA Clones

Phage DNA from λgt11 f 1 clones was prepared by a rapid isolation procedure. Clarified phage plate lysate (1 ml) was mixed with 270 of 25% wt/vol polyethylene glycol (PEG 6000) in 2.5M NaCl and incubated at room temperature for 15 min. The mixture was then spun for 5 min in a microfuge (Eppendorf, FRG), and the supernatant was removed. The pellet was dissolved in 100 μL of 10 mM Tris/HCl pH8.0 containing 1 mM EDTA and 100 mM NaCl (TE). This DNA preparation was extracted with phenol/TE, the phenol phase was washed with 100 μl TE, the pooled aqueous phases were then extracted another 2 times with phenol/TE, 2 times with Leder phenol (phenol/chloroform/isoamylalcohol; 25:24:1), once with chloroform and the DNA was precipitated by ethanol.

DNA Sequencing

To obtain clones for DNA sequence analysis, the λgt11 fl phage DNA was digested with EcoRI restriction enzyme (Pharmacia, Uppsala, Sweden) and the DNA insert was ligated to EcoRI-digested M13-derived sequencing vectors mp18 and mp19 (Maniatis, T. et al., *Molecular Cloning: A Laboratory Manual,* Cold Spring Harbor Laboratory Press (1982)). Transformation was carried out using *E. coli* TG-1 and sequencing was performed by the dideoxynucleotide chain termination method (Sanger, F. et al,, *Proc. Natl. Acad. Sci. U.S.A.,* 74:5463–5467 (1977)) using the Sequenase version 2.0 DNA sequencing kit (U.S.B., Cleveland, Ohio).

Polymerase Chain Reaction (PCR)

PCR was performed by the Taq DNA polymerase method (Saiki, R. K. et al., *Science* 239:487–491 (1988)) using the TaqPaq kit (Biotech International, Bentley, Wash.) and the conditions recommended by the supplier with 10 ng of target DNA and 10 pmol of λgt11 primers (New England BioLabs, Beverly, Mass.).

RESULTS

Isolation of *Der f* I cDNA Clones

Two clones expressing the major mite allergen *Der f* I were isolated from the *D. farinae* cDNA λgt11 library by their ability to hybridize with both of the *Der p* I cDNA probes (nucleotides 1–348 and 349–857). This approach was adopted because amino acid sequencing had shown high homology (80%) between these two allergens (Thomas, W. R., et al., *Advances in the Biosciences.,* 14.:139–147 (1989)). Digestion of the λgt11 fl clone DNA with EcoRI restriction enzyme to release the cDNA insert produced three *Der f* I cDNA EcoRI fragments: one approximately 800 bases long and a doublet approximately 150 bases long. The *Der f* I cDNA insert was also amplified from the phage DNA by the polymerase chain reaction (PCR) resulting in a PCR product of approximately 1.1-kb. Each *Der f* I cDNA fragment was cloned separately into the M13-derived sequencing vectors mp18 and mp19 and sequenced.

DNA Sequence Analysis

The nucleotide sequence of *Der f* I cDNA was determined using the sequencing strategy shown in FIG. 9. The complete sequence was shown to be 1084 bases long and included a 335-base long 5' proximal end sequence, a coding region for the entire native *Der f* I protein of 223 amino acids with a derived molecular weight of 25,191 and an 80-base long 3' noncoding region (FIG. 10). The assignment of the threonine residue at position 1 as the $NH_2$-terminal amino acid of *Der f* I was based on data obtained by $NH_2$-terminal amino acid sequencing of the native protein and the predicted amino acid sequence of recombinant *Der p* I (Chua, K. Y. et al., *J. Exp. Med.,* 167:175–182 (1988)). The predicted amino acid sequence of the *Der f* I cDNA in the NH₂-terminal region matched completely with that determined at the protein level (FIG. 10).

The complete mature protein coded by a single open reading frame terminating at the TGA stop codon at nucleotide position 42-44 is presumed to be the translation initiation site since the subsequent sequence codes for a typical signal peptide sequence.

Amino Acid Sequence Analysis

The amino acid sequence of Der f I predicted by nucleotide analysis is shown in FIG. 10. As shown in the composite alignment of the amino acid sequence of mature Der p I and Der f I (FIG. 11), high homology was observed between the two proteins. Sequence homology analysis revealed that the Der f I protein showed 81% homology with the Der p I protein as predicted by previous conventional amino acid sequencing. In particular, the residues making up the active side of Der p I, based on those determined for papain, actinidin, cathepsin H, and cathepsin B, are also conserved in the Der f I protein. The residues are glutamine (residue 29), glycine, serine and cysteine (residues 33-35), histidine (residue 171) and asparagine, serine and tryptophan (residues 191-193) where the numbering refers to Der f I. The predicted mature Der f I amino acid sequence contains a potential N-glycosylation site (Asn-Thr-Ser) at position 53-55 which is also present as Asn-Gln-Ser at the equivalent position in Der p I.

Analysis of the predicted amino acid sequence of the entire Der f I cDNA insert has shown that, as for other cysteine proteases (FIG. 12), the Der f I protein has pre- and proform intermediates. As previously mentioned, the methionine residue at position −98 is presumed to be the initiation methionine. This assumption is based on the fact that firstly, the 5' proximal end sequence from residues −98 to −81 is composed predominantly of hydrophobic amino acid residues (72%), which is the characteristic feature of signal peptides (Von Heijne, G., *EMBO J.*, 3:2315-2323 (1984)). Secondly, the lengths of the presumptive pre- (18 amino acid residues) and pro-peptides (80 residues) are similar to those for other cysteine proteases (FIG. 12). Most cysteine proteases examined have about 120 preproenzyme residues (of which an average of 19 residues form the signal peptide) with cathepsin B the smallest with 80 (Ishidoh, K. et al., *FEBS Letters*, 22.6:32-37 (1987)). Der f I falls within this range with a total of 98 preproenzyme residues.

By following the method for predicting signal-sequence cleavage sites outlined in Von Heijne, it is proposed that cleavage from the pre-Der f I sequence for proenzyme formation occurs at the signal peptidase cleavage site lying between Ala (−81) and Arg (−80) (Von Heijne, G., *Eur. J. Biochem.*, 133:17-21 (1988) and *J. Mol. Biol.*, 184:99-105 (1985)). Thus, the sequence from residues −98 to −81 codes for the leader peptide while the proenzyme moiety of Der f I begins at residue Arg (−80) and ends at residue Glu (−1).

EXAMPLE 7

Isolation and Characterization of cDNA Coding for Der f II

MATERIALS AND METHODS

Amino Acid Sequence Analysis

Preparation of λgt11 *D. farinae* cDNA Ligations

*D. farinae* was purchased from Commonwealth Serum Laboratories, Parkville, Australia, and used to prepare mRNA (polyadenylated RNA) as described (Stewart, G. A. and W. R. Thomas, *Int. Arch. Allergy Appl Immunol.*, 83:384-389 (1987)). The mRNA was suspended at approximately 0.5 µg/µl and 5 µg used to prepare cDNA by the RNase H method (Gubler, U. and Hoffman, B. J., *Gene*, 25:263-269 (1983)) using a kit (Amersham International, Bucks). EcoRI linkers (Amersham, GGAATTCC) were attached according to the method described by Huynh et al., Constructing and screening cDNA libraries in gt10 and gt11, In: Glover, DNA Cloning vol. A practical approach pp. 47-78 IRL Press, Oxford (1985)). The DNA was then digested with EcoRI and recovered from an agarose gel purification by electrophoresis into a DEAE membrane (Schleicher and Schuell, Dassel, FRG, NA-45) according to protocol 6.24 of Sambrook et al., (Sambrook et al., Molecular Cloning: A Laboratory Manual, 2d Ed., Cold Spring Harbor Laboratory Press (1989)), except 0.5M arginine base was used for elution. The cDNA was then ligated in λgt10 and λgt11 at an arms to insert ratio of 2:1. Some was packaged for plaque libraries and an aliquot retained for isolating sequences by polymerase chain reaction as described below.

Isolation of Der f II CDNA by Polymerase Chain Reaction

To isolate Der f II cDNA, an oligonucleotide primer based on the N-terminal sequence of Der p II was made because their amino acid residues are identical in these regions (Heymann, P. W. et al., *J. Allergy Clin. Immunol.*, 83:1055-1087 (1989)). The primer GGATC-CGATCAACTCGATGC-3' was used. The first GGATCC encodes a BamH1 site and the following sequence GAT ... encodes the first four residues of Der p II. For the other primer the λgt11 TTGACAC-CAGACCAACTGGTAATG-3' reverse primer flanking the EcoRI cloning site was used (New England Biolabs, Beverly, Mass.). The Der p II primer was designed to have approximately 50-60% G-C and to end on the first or second, rather than the third, base of a codon (Gould, S. J. et al., *Proc. Natl. Acad. Sci.*, 86:1934-1938 (1989); Summer, R. and D. Tautz, *Nucleic Acid Res.*, 17:6749 (1989)).

The PCR reactions were carried out in a final reaction volume of 25 µl containing 67 mM Tris-HCL (pH8.8 at 25° C.), 16.6 mM (NH₄)₂SO₄, 40 µM dNTPs, 5 mM 2-mercaptoethanol, 6 µM EDTA, 0.2 mg/ml gelatin, 2 mM MgCl₂, 10pmoles of each primer and 2 units of Taq polymerase. Approximately 0.001 µg of target DNA was added and the contents of the tube were mixed and overlayed with paraffin oil. The tubes were initially denatured at 95° C. for 6 minutes, then annealed at 55° C. for 1 minute and extended at 72° C. for 2 minutes. Thereafter for 38 cycles, denaturing was carried out for 30 seconds and annealing and extension as before. In the final (40th) cycle, the extension reaction was increased to 10 minutes to ensure that all amplified products were full length. The annealing temperature was deliberately set slightly lower than the Tm of the oligonucleotide primers (determined by the formula Tm=69.3+0.41 (G+C%)-650/oligo length) to allow for mismatches in the N-terminal primer.

5 µl of the reaction was then checked for amplified bands on a 1% agarose gel. The remainder of the reaction mixture was extracted with chloroform to remove all of the paraffin oil and ethanol precipitated prior to purification of the amplified product on a low melting point agarose gel (Bio-Rad, Richmond, Calif.).

Subcloning of PCR Product

The ends of the purified PCR product were filled in a reaction containing 10 mM Tris HCl, 10 mM MgCl$_2$, 50 mM NaCl, 0.025 mM dNTP and 1 μl of Klenow enzyme in a final volume of 100 μl. The reaction was carried out at 37° C. for 15 minutes and heat inactivated at 70° C. for 10 minutes. The mixture was Leder phenol extracted before ethanol precipitation. The resulting blunt ended DNA was ligated into M13mp118 digested with Sma I in a reaction containing 0.5M ATP, 1 X ligase buffer and 1 unit of T$_4$ ligase at 15° C. for 24 hrs and transformed into *E. coli* TG1 made competent by the CaCl$_2$ method. The transformed cells were plated out as a lawn on L+G plates and grown overnight at 37° C.

Preparation of Single-Stranded DNA Template for Sequencing

Isolated white plaques were picked using an orange stick into 2.5 ml of an overnight culture of TG1 cells diluted 1 in 100 in 2 X TY broth, and grown at 37° C. for 6 hours. The cultures were pelleted and the supernatant removed to a fresh tube. To a 1 ml aliquot of this supernatant 270 μl of 20% polyethylene glycol, 2.5M NaCl was added and the tube was vortexed before allowing it to stand at room temperature (RT) for 15 minutes. This was then spun down again and all traces of the supernatant were removed from the tube. The pellet was then resuspended in 100 μl of 1 X TE buffer. At least 2 phenol:TE extractions were done, followed by 1 Leder phenol extraction and a CHCl$_3$ extraction. The DNA was precipitated in ethanol and resuspended in a final volume of 20μl of TE buffer.

DNA Analysis

DNA sequencing was performed with the dideoxynucleotide chain termination (Sanger, F. et al., *Proc. Natl. Acad, Sci.*, 74:5463–5467 (1977)) using DNA produced from M13 derived vectors mp18 and mp19 in *E. coli* TG1 and T4 DNA polymerase (Sequenase version 2.0, USB Corp., Cleveland, Ohio; Restriction endonucleases were from Toyobo, (Osaka, Japan). All general procedures were by standard techniques (Sambrook, J. et al., A Laboratory Manual, 2d Ed. Cold Spring Harbor Laboratory Press (1989)). The sequence analysis was performed using the Mac Vector Software (IBI, New Haven, Conn.).

RESULTS

*D. farinae* cDNA ligated in λgt11 was used to amplify a sequence using an oligonucleotide primer with homology to nucleotides coding for the 4 N-terminal residues of *Der p* II and a reverse primer for the λgt11 sequence flanking the coding site. Two major bands of about 500 bp and 300 bp were obtained when the product was gel electrophoresed. These were ligated into M13 mp18 and a number of clones containing the 500 bp fragment were analyzed by DNA sequencing. Three clones produced sequence data from the N-terminal primer end and one from the other orientation. Where the sequence data from the two directions overlapped, a complete match was found. One of the clones read from the N-terminal primer, contained a one-base deletion which shifted the reading frame. It was deduced to be a copying error, as the translated sequence from the other two clones matched the protein sequence for the first 20 amino acid residues of the allergen.

Figure 17A:
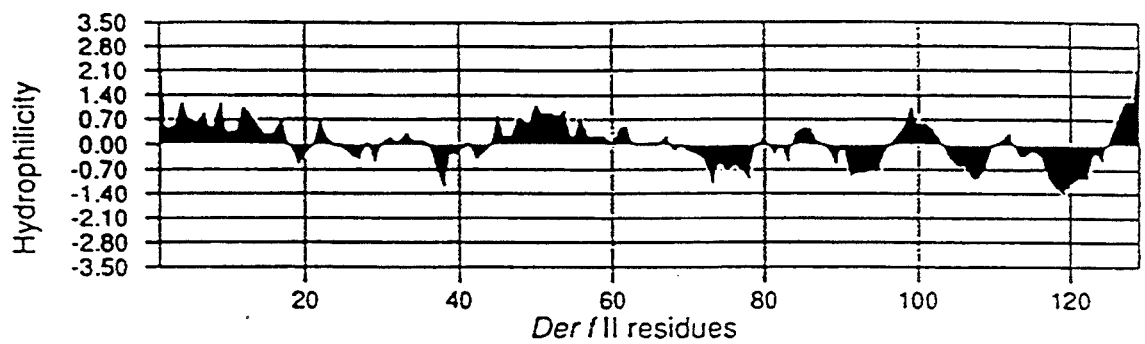
FIG. 17 is a hydrophilicity plot of *Der f* II and *Der p* II using the Hopp-Woods algorithm computed with the Mac Vector Sequence Analysis Software (IBI, New Haven) using a 6-residue window.
Figure 17B:
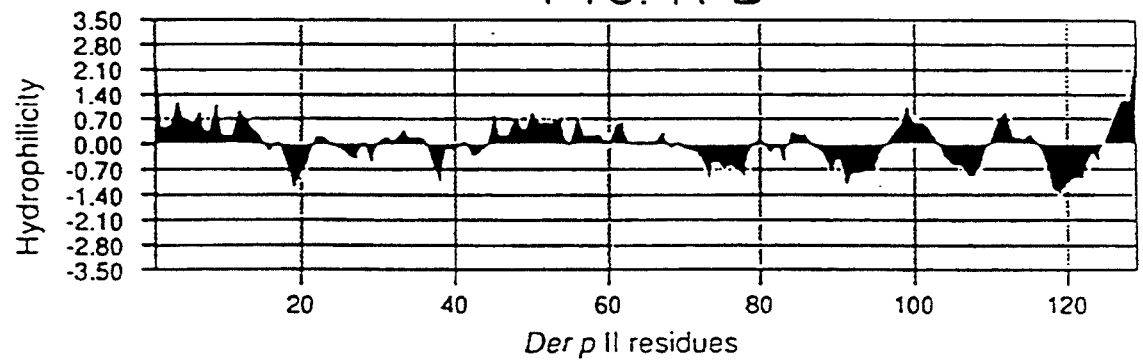

The sequence of the clones showing consensus and producing a correct reading frame is shown in FIG. 14, along with the inferred amino acid sequence. It coded for a 129 residue protein with no N-glycosylation site and a calculated molecular weight of 14,021 kD. No homology was found when compared to other proteins on the GenBank data base (61.0 release). It did, however, show 88% amino acid residue homology with *Der p* II shown in the alignment in FIG. 16. Seven out of the 16 changes were conservative. The conserved residues also include all the cysteines present at positions 8, 21, 27, 73 and 119. There was also considerable nucleotide homology, although the restriction enzyme map generated from the sequence data for commonly used enzymes is different from *Der p* II (FIG. 15). The hydrophobicity plots of the translated sequence of *Der f* II and *Der p* II shown in FIG. 17 are almost identical.

EXAMPLE 8

Determination of Nucleotide Sequence Polymorphisms in the *Der p* I, *Der p* II and *Der f* II Allergens It was expected that there were sequence polymorphisms in the nucleic acid sequence coding for *Der p* I, *Der p* II, *Der f* I and *Der f* II, due to natural allelic variation among individual mites. Several nucleotide and resulting amino acid sequence polymorphisms were discovered during the sequencing of different *Der p* I, *Der p* II and *Der f* II clones. The amino acid sequence polymorphisms are shown in FIGS. 18, 19 and 20.

The original *Der p* I λgt11 cDNA library was reprobed with cDNA obtained from the λgt11 pI(13T) clone to identify new clones. Similarly, the λgt11 cDNA library of *Der p* II was reprobed with cDNA obtained from the λgt11 pII(C1) clone to identify additional *Der p* II clones. These clones were isolated, sequenced and found to contain nucleotide and resulting amino acid sequence polymorphisms (see FIG. 18 and 19).

Four *Der p* I clones, (b), (c), (d) and (e) were sequenced, as shown in FIG. 18. Clone *Der p* I(d) was found to contain the following polymorphisms relative to the clone *Der p* I(a) sequence: (1) the codon for amino acid residue 136 was ACC rather than AGC, which results in a predicted amino acid substitution of Thr for Ser; (2) the codon for amino acid residue 149 had a silent mutation, GCT rather than GCA; and (3) the codon for amino acid residue 215 was CAA rather than GAA; which results in a predicted amino acid substitution of Gln for Glu.

The *Der p* II clones, *Der p* II(1) and *Der p* II(2) were sequenced as shown in FIG. 19. Clone *Der p* II(2) was found to have the codon TCA, rather than ACA at amino acid residue 47, which results in a predicted amino acid substitution of Ser for Thr. This clone also was found to have the codon AAT at amino acid residue 113 rather than GAT, which results in a predicted amino acid substitution of Asn for Asp. The codon for amino acid 127 of this clone was found to be CTC rather than ATC. This change in codon 127 results in a predicted amino acid substitution of Leu for Ile.

Additional *Der f* II cDNA clones containing nucleic acid and resulting amino acid sequence polymorphisms were obtained from PCR reactions using cDNA prepared with RNA isolated from *D. farinae* mites (Commonwealth Serum Laboratories, Parksville, Australia).

cDNA was prepared and ligated in λgt10 as previously described (Trudinger et al. (1991) *Clin. Exp. Allergy* 21:33–37). The clones described below were isolated following PCR of the λgt10 library using a 5' primer, which had the sequence 5'-GGATCCGATCAAGT-CGATGT-3'. The nucleotides 5'-GGATCC-3' of the 5' primer correspond to a Bam HI endonuclease site added for cloning purposes. The remaining nucleotides of the 5' primer, 5'-GATCAAGTCGATGT-3' correspond to the first 4 amino acids of *Der p* II (Chua et al. (1990) *Int. Arch. Allergy Clin. Immunol.* 91:118–123) as described in Trudinger et al, ((1991) *Clin. Exp. Allergy* 21:33–37). The 3' primer, which has the sequence 5'-TTGACAC-CAGACCAACTGGTAATG-3', corresponds to a sequence of the λgt10 cloning vector (Trudinger et al. supra).

PCR was performed as described (Trudinger et al. supra) and four *Der f* II clones, MT3, MT5, MT16 and MT18, were sequenced, as shown in FIG. 20. Three clones were sequenced that had potential polymorphisms relative to the published *Der f* II sequence (Trudinger et al. supra). The codon for amino acid 52 of clone MT18 was ATT rather than the published ACT (Trudinger et al. supra). This change in codon 52 of clone MT18 would result in a predicted amino acid change from Thr to Ile. Clone MT5 contained three changes from the published sequence (Trudinger et al. supra): (1) the codon for amino acid 11 was AGC rather than the published AAC (Trudinger et al. supra), which results in a predicted amino acid substitution of Ser for Asn; (2) the codon for amino acid 52 was ATT, rather than the published ACT (Trudinger et al. supra.), which results in a predicted amino acid substitution of Ile for Thr; and (3) the codon for amino acid 88 was ATC rather than the published GCC (Trudinger et al. supra), which results in a predicted amino acid substitution of Ile for Ala. Clone MT16 had a silent mutation in the codon for amino acid 68 (ATC versus the published ATT (Trudinger et al,. supra) that did not change the predicted amino acid at this residue. The following substitutes were also observed by Yuuki et al., (*Jpn.J.Allergol.* 6:557–561, 1990); Ile at residue 52, Ile at residue 54 and Ile at residue 88.

Equivalents

Those skilled in the art will recognize, or be able to ascertain using no more than routine experimentation, many equivalents to the specific embodiments of the invention described herein. Such equivalents are intended to be encompassed by the following claims.

REFERENCES

1. Ford, A. W., Rawle, F. C., Lind, P., Spieksma, F. T. M., Lowenstein, H., Platts-Mills, T. A. E. (1985). Standardization of *Dermatophagoides pteronyssinus*. Assessment of potency and allergen content in the coded extracts. *Int. Arch. Allergy Appl. Immunol.* 76:58–67.
2. Lind, P., Lowenstein, H. (1983). Identification of allergens in *Dermatophagoides pteronyssinus* mite body extract by crossed radioimmunelectrophoresis with two different rabbit antibody pools. *Scand. J. Immunol.* 17:263–273.
3. Krilis, S., Baldo, B. A., Basten, A. (1984). Antigens and allergens from the common house dust mite *Dermatophagoides pteronyssinus* Part II. Identification of the major IgE binding antigens by crossed radioimmuno-electrophoresis. *J. Allergy Clin. Immunol.* 74:1 42–146.
4. Tovey, E. R., Chapman, M. D., Platts-Mills, T. A. E. (1981). Mite faeces are a major source of house dust allergens. *Nature* 289:592–593.
5. Gubler, U., Hoffman, B. J. (1983). A simple and very efficient method for generating cDNA libraries. *Gene* 25:263–269.
6. Huynh, T. V., Young, R. A., Davis, R. W. Constructing and screening cDNA libraries in λ10 and λgt11. p48–78 in DNA Cloning Col. 1, A practical approach. Ed. D. M. Glover, IRL press.
7. Stewart, G. A., Thomas, W. R. (1987). In vitro translation of messenger RNA from the house mite *Dermatophagoides pteronyssinus*. *Int. Arch. Allergy Appl. Immunol.* 83:384–389.
8. Thomas, W. R., Rossi, A. A. (1986). Molecular cloning of DNA coding for outer membrane proteins of *Haemophilus influenzae* type b. *Infection and Immunity* 52:812–817.
9. Simpson, R. J., Smith, J. A., Mortiz, R. L., O'Hare, M. J., Rudland, P. S., Morrison, J. R., Lloyd, C. J., Grego, B., Burgess, A. W. and Nice, E. L. (1985). Rat Epidermal Growth Factor: Complete amino acid sequence. *Eur. J. Biochem.* 153:629–637.
10. Maniatis, T., Fritsch, E. F., Sambrook, J. (1982). Molecular cloning. A Laboratory Manual, Cold Spring Harbor Laboratory.
11. Sanger, F., Nicklen, S., Coulson, A. R. (1977). DNA sequencing with chain-terminating inhibitors. *Proc. Natl. Acad. Sci.* 74:5463–5467.
12. Heyman, P. W., Chapman, M. D., Platts-Mills, T. A. E. (1986). Antigen *Der f* I from the house dust mite *Dermatophagoides farinae*: Structural comparison with *Der p* I from *Dermatophagoides pteronyssinus* and epitope specificity of murine IgG and human IgE antibodies. *J. Immunol.* 137:2841–2847.
13. Voorhorst, R., Spieksma-Boezeman, M. I. A., and Spieksma, F. Th.M. (1964). Is a mite (Dermatophagoides sp) the producer of the house dust allergen. *Allerg. Asthma.* 10:329.
14. Voorhorst, R., Spieksma, F. Th. M., Varekamp, H., Leupen, M. J. and Lyklema, A. W., (1967). The house dust mite (*Dermatophagoides pteronyssinus*) and the allergens it produces. Identity with the house dust allergen. *J. Allergy.* 39:325.
15. Stewart, G. A. and Thomas, W. R. (1987). In vitro translation of messenger RNA from the house dust mite *Dermatophagoides pteronyssinus*. *Int. Arch. Allergy Appl. Immunol.* 83:384.
16. Messing, J. (1983). New M13 vectors for cloning. *Methods Enzymol.* 101:20.
17. Stewart, G. A., Simpson, R. J., Thomas, W. R. and Turner, K. J. (1986). The physiochemical characterization of a major protein allergen from the house dust mite, EP. *Asian Pac. J. Allergy Immunol.* 5:71.
18. Kozak, M. (1984). Compilation and analysis of sequences upstream from the translational start site in eukaryotic mRNAs. *Nucleic. Acids Res.* 12:857.
19. San Segundo, B., Chain, S. J. and Steiner, D. F. (1985). Identification of cDNA clones encoding a precursor of rat liver cathepsin B. *Proc. Natl. Acad. Sci. U.S.A.* 82:2320.
20. Portnoy, D. A., Erickson, A. H., Kochan, J., Ravetch, J. V. and Unkeless, J. C. (1986). Cloning and characterization of a mouse cysteine proteinase. *J. Biol. Chem.* 261:14697.

21. Williams, J. G., North, M. J. and Mahbubani, H. (1985). A developmentally regulated cysteine proteinase in *Dictyostelium discoideum. EMBO (Eur. Mol. Biol. Organ.) J.* 4:999.
22. Hopp, T. P. (1986). Protein surface analysis. Method for identifying antigenic determinants and other interaction sites. *J. Immunol. Methods*, 88:1.
23. Von Heijne, G. (1984). Analysis of the distribution of charged residues in the N-terminal region of signal sequences: implications of protein export in prokaryotic and eukaryotic cells. *EMBO (Eur. Mol. Biol. Organ.) J.* 3:2315.
24. Ullrich, A., Shine, J., Chirgwin, J., Pictet, R., Tischer, E., Rutter, W. J. and Goodman, H. W. (1977). Rat insulin genes: Construction of plasmids containing th coding sequences. *Science* (Wash. DC) 196:1313.
25. Carne, T. and Scheele, G. (1985). Cell Biology of the Secretory Process. M.Cantin, editor. S. Karger AG, Basel. 73.
26. Smith, D. and Johnson (1988), *Gene* (in press).
27. Thomas, W. R. and Rossi, A. A. (1986). Molecular cloning of DNA coding for outer membrane proteins of *Haemophilus influenzae* Type b. *Infection and Immunity* 52:812–817.
28. Thomas, W. R., Stewart, G. A., Simpson, R. J., Chua, K. Y., Plozza, T. M., Dilworth, Dr. U., Nisbet, A. and Turner, K. J. (1987). Cloning and expression of DNA coding for the major house dust mite allergen *Der p* I in *Escherichia coli. Int. Arch. Allergy Appl. Immunol.* 85:127–129.
29. Stewart, G. A.. and Holt, P. G. (1987). Immunogenicity and tolerogenicity of a major house dust mite allergen *Der p* I. *Int. Arch. Allergy Appl. Immunol.* 83:44–51.
31. Chapman, M. D., Heymann, P. W. and Platts-Mills, T. A. E. (1987). Mite allergens 1. Epitope mapping of major dust mite (Dermatophagoides) allergens using monoclonal antibodies. Mite Allergy—A World Wide Problem. Ed. A. L. deWeck and A. Todt. The UCB Institute of Allergy.

---

We claim:

1. An isolated protein allergen of *Der p* I consisting of the amino acid sequence:

Thr Asn Ala Cys Ser Ile Asn Gly Asn Ala Pro Ala Glu
Ile Asp Leu Arg Gln Met Arg Thr Val Thr Pro Ile Arg
Met Gln Gly Gly Cys Gly Ser Cys Trp Ala Phe Ser Gly
Val Ala Ala Thr Glu Ser Ala Tyr Leu Ala $Xaa_1$ Arg Asn
Gln Ser Leu Asp Leu Ala Glu Gln Glu Leu Val Asp Cys
Ala Ser Gln His Gly Cys His Gly Asp Thr Ile Pro Arg
Gly Ile $Xaa_2$ Tyr Ile Gln His Asn Gly Val Val Gln Glu
Ser Tyr Tyr Arg Tyr Val Ala Arg Glu Gln Ser Cys Arg
Arg Pro Asn Ala Gln Arg Phe Gly Ile Ser Asn Tyr Cys
Gln Ile Tyr Pro Pro Asn Xaa$_3$ Asn Lys Ile Arg Glu Ala
Leu Ala Gln Thr His Xaa$_4$ Ala Ile Ala Val Ile Ile Gly
Ile Lys Asp Leu Asp Ala Phe Arg His Tyr Asp Gly Arg
Thr Ile Ile Gln Arg Asp Asn Gly Tyr Gln Pro Asn Tyr
His Ala Val Asn Ile Val Gly Tyr Ser Asn Ala Gln Gly
Val Asp Tyr Trp Ile Val Arg Asn Ser Trp Asp Thr Asn
Trp Gly Asp Asn Gly Tyr Gly Tyr Phe Ala Ala Asn Ile
Asp Leu Met Met Ile Glu Xaa$_5$ Tyr Pro Tyr Val Val Ile
Leu where $Xaa_1$ is selected from the group consisting of His and Tyr;

where $Xaa_2$ is selected from the group consisting of Glu and Lys;

where $Xaa_3$ is selected from the group consisting of Ala and Val;

where $Xaa_4$ is selected from the group consisting of Ser and Thr; and where $Xaa_5$ is selected from the group consisting of Glu and Gln, except for the amino acid sequence where $Xaa_1$ is His, $Xaa_2$ is Glu, $Xaa_3$ is Ala, $Xaa_4$ is Ser and $Xaa_5$ is Glu.

2. A therapeutic composition comprising a protein allergen of claim 1 and a pharmaceutically acceptable carrier or diluent.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 834 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..738

( x i ) SEQUENCE DESCRIPTION: SEQ ID NO:1:

```
AAA  AAC  CGA  TTT  TTG  ATG  AGT  GCA  GAA  GCT  TTT  GAA  CAC  CTC  AAA  ACT         48
Lys  Asn  Arg  Phe  Leu  Met  Ser  Ala  Glu  Ala  Phe  Glu  His  Leu  Lys  Thr
-23            -20                      -15                      -10

CAA  TTC  GAT  TTG  AAT  GCT  GAA  ACT  AAC  GCC  TGC  AGT  ATC  AAT  GGA  AAT         96
Gln  Phe  Asp  Leu  Asn  Ala  Glu  Thr  Asn  Ala  Cys  Ser  Ile  Asn  Gly  Asn
          -5                       -1    1                  5

GCT  CCA  GCT  GAA  ATC  GAT  TTG  CGA  CAA  ATG  CGA  ACT  GTC  ACT  CCC  ATT        144
Ala  Pro  Ala  Glu  Ile  Asp  Leu  Arg  Gln  Met  Arg  Thr  Val  Thr  Pro  Ile
10                       15                  20                       25

CGT  ATG  CAA  GGA  GGC  TGT  GGT  TCA  TGT  TGG  GCT  TTC  TCT  GGT  GTT  GCC        192
Arg  Met  Gln  Gly  Gly  Cys  Gly  Ser  Cys  Trp  Ala  Phe  Ser  Gly  Val  Ala
                    30                       35                       40

GCA  ACT  GAA  TCA  GCT  TAT  TTG  GCT  CAC  CGT  AAT  CAA  TCA  TTG  GAT  CTT        240
Ala  Thr  Glu  Ser  Ala  Tyr  Leu  Ala  His  Arg  Asn  Gln  Ser  Leu  Asp  Leu
               45                       50                  55

GCT  GAA  CAA  GAA  TTA  GTC  GAT  TGT  GCT  TCC  CAA  CAC  GGT  TGT  CAT  GGT        288
Ala  Glu  Gln  Glu  Leu  Val  Asp  Cys  Ala  Ser  Gln  His  Gly  Cys  His  Gly
               60                       65                  70

GAT  ACC  ATT  CCA  CGT  GGT  ATT  GAA  TAC  ATC  CAA  CAT  AAT  GGT  GTC  GTC        336
Asp  Thr  Ile  Pro  Arg  Gly  Ile  Glu  Tyr  Ile  Gln  His  Asn  Gly  Val  Val
     75                       80                  85

CAA  GAA  AGC  TAC  TAT  CGA  TAC  GTT  GCA  CGA  GAA  CAA  TCA  TGC  CGA  CGA        384
Gln  Glu  Ser  Tyr  Tyr  Arg  Tyr  Val  Ala  Arg  Glu  Gln  Ser  Cys  Arg  Arg
90                       95                  100                      105
```

|     |     |     |     |     |     |     |     |     |     |     |     |     |     |     |     |     |
|---|---|---|---|---|---|---|---|---|---|---|---|---|---|---|---|---|
| CCA | AAT | GCA | CAA | CGT | TTC | GGT | ATC | TCA | AAC | TAT | TGC | CAA | ATT | TAC | CCA | 432 |
| Pro | Asn | Ala | Gln | Arg | Phe | Gly | Ile | Ser | Asn | Tyr | Cys | Gln | Ile | Tyr | Pro | |
|     |     |     | 110 |     |     |     |     | 115 |     |     |     |     |     | 120 |     |     |
| CCA | AAT | GCA | AAC | AAA | ATT | CGT | GAA | GCT | TTG | GCT | CAA | ACC | CAC | AGC | GCT | 480 |
| Pro | Asn | Ala | Asn | Lys | Ile | Arg | Glu | Ala | Leu | Ala | Gln | Thr | His | Ser | Ala | |
|     |     |     |     | 125 |     |     |     | 130 |     |     |     |     |     | 135 |     |     |
| ATT | GCC | GTC | ATT | ATT | GGC | ATC | AAA | GAT | TTA | GAC | GCA | TTC | CGT | CAT | TAT | 528 |
| Ile | Ala | Val | Ile | Ile | Gly | Ile | Lys | Asp | Leu | Asp | Ala | Phe | Arg | His | Tyr | |
|     |     | 140 |     |     |     |     | 145 |     |     |     |     |     | 150 |     |     |     |
| GAT | GGC | CGA | ACA | ATC | ATT | CAA | CGC | GAT | AAT | GGT | TAC | CAA | CCA | AAC | TAT | 576 |
| Asp | Gly | Arg | Thr | Ile | Ile | Gln | Arg | Asp | Asn | Gly | Tyr | Gln | Pro | Asn | Tyr | |
|     | 155 |     |     |     |     | 160 |     |     |     |     | 165 |     |     |     |     |     |
| CAC | GCT | GTC | AAC | ATT | GTT | GGT | TAC | AGT | AAC | GCA | CAA | GGT | GTC | GAT | TAT | 624 |
| His | Ala | Val | Asn | Ile | Val | Gly | Tyr | Ser | Asn | Ala | Gln | Gly | Val | Asp | Tyr | |
| 170 |     |     |     |     | 175 |     |     |     |     | 180 |     |     |     |     | 185 |     |
| TGG | ATC | GTA | CGA | AAC | AGT | TGG | GAT | ACC | AAT | TGG | GGT | GAT | AAT | GGT | TAC | 672 |
| Trp | Ile | Val | Arg | Asn | Ser | Trp | Asp | Thr | Asn | Trp | Gly | Asp | Asn | Gly | Tyr | |
|     |     |     |     | 190 |     |     |     |     | 195 |     |     |     |     | 200 |     |     |
| GGT | TAT | TTT | GCT | GCC | AAC | ATC | GAT | TTG | ATG | ATG | ATT | GAA | GAA | TAT | CCA | 720 |
| Gly | Tyr | Phe | Ala | Ala | Asn | Ile | Asp | Leu | Met | Met | Ile | Glu | Glu | Tyr | Pro | |
|     |     |     | 205 |     |     |     |     | 210 |     |     |     |     | 215 |     |     |     |
| TAT | GTT | GTC | ATT | CTC | TAAACAAAAA | GACAATTTCT | TATATGATTG | TCACTAATTT | 775 |
| Tyr | Val | Val | Ile | Leu | | | | | |
|     |     |     | 220 |     | | | | | |

ATTTAAAATC AAAATTTTTT AGAAAATGAA TAAATTCATT CACAAAAATT AAAAAAAAA    834

(2) INFORMATION FOR SEQ ID NO:2:

(i) SEQUENCE CHARACTERISTICS:
        (A) LENGTH: 245 amino acids
        (B) TYPE: amino acid
        (D) TOPOLOGY: linear (ii) MOLECULE TYPE: protein (xi) SEQUENCE DESCRIPTION: SEQ ID NO:2:

| Lys | Asn | Arg | Phe | Leu | Met | Ser | Ala | Glu | Ala | Phe | Glu | His | Leu | Lys | Thr |
|---|---|---|---|---|---|---|---|---|---|---|---|---|---|---|---|
| −23 | | | −20 | | | | | −15 | | | | | −10 | | |
| Gln | Phe | Asp | Leu | Asn | Ala | Glu | Thr | Asn | Ala | Cys | Ser | Ile | Asn | Gly | Asn |
| | | −5 | | | | | −1 | 1 | | | | 5 | | | |
| Ala | Pro | Ala | Glu | Ile | Asp | Leu | Arg | Gln | Met | Arg | Thr | Val | Thr | Pro | Ile |
| 10 | | | | | 15 | | | | 20 | | | | | | 25 |
| Arg | Met | Gln | Gly | Gly | Cys | Gly | Ser | Cys | Trp | Ala | Phe | Ser | Gly | Val | Ala |
| | | | 30 | | | | | 35 | | | | | | 40 | |
| Ala | Thr | Glu | Ser | Ala | Tyr | Leu | Ala | His | Arg | Asn | Gln | Ser | Leu | Asp | Leu |
| | | | 45 | | | | | 50 | | | | | | 55 | |
| Ala | Glu | Gln | Glu | Leu | Val | Asp | Cys | Ala | Ser | Gln | His | Gly | Cys | His | Gly |
| | | 60 | | | | | 65 | | | | | 70 | | | |
| Asp | Thr | Ile | Pro | Arg | Gly | Ile | Glu | Tyr | Ile | Gln | His | Asn | Gly | Val | Val |
| | 75 | | | | | 80 | | | | | 85 | | | | |
| Gln | Glu | Ser | Tyr | Tyr | Arg | Tyr | Val | Ala | Arg | Glu | Gln | Ser | Cys | Arg | Arg |
| 90 | | | | | 95 | | | | | 100 | | | | | 105 |
| Pro | Asn | Ala | Gln | Arg | Phe | Gly | Ile | Ser | Asn | Tyr | Cys | Gln | Ile | Tyr | Pro |
| | | | 110 | | | | | 115 | | | | | | 120 | |
| Pro | Asn | Ala | Asn | Lys | Ile | Arg | Glu | Ala | Leu | Ala | Gln | Thr | His | Ser | Ala |
| | | | | 125 | | | | 130 | | | | | | 135 | |
| Ile | Ala | Val | Ile | Ile | Gly | Ile | Lys | Asp | Leu | Asp | Ala | Phe | Arg | His | Tyr |
| | | 140 | | | | | 145 | | | | | | 150 | | |
| Asp | Gly | Arg | Thr | Ile | Ile | Gln | Arg | Asp | Asn | Gly | Tyr | Gln | Pro | Asn | Tyr |
| | 155 | | | | | 160 | | | | | 165 | | | | |

```
His  Ala  Val  Asn  Ile  Val  Gly  Tyr  Ser  Asn  Ala  Gln  Gly  Val  Asp  Tyr
170            175                      180                      185

Trp  Ile  Val  Arg  Asn  Ser  Trp  Asp  Thr  Asn  Trp  Gly  Asp  Asn  Gly  Tyr
               190                      195                      200

Gly  Tyr  Phe  Ala  Ala  Asn  Ile  Asp  Leu  Met  Met  Ile  Glu  Glu  Tyr  Pro
               205                      210                      215

Tyr  Val  Val  Ile  Leu
               220
```

( 2 ) INFORMATION FOR SEQ ID NO:3:

( i ) SEQUENCE CHARACTERISTICS:
        ( A ) LENGTH: 588 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 69..509

( x i ) SEQUENCE DESCRIPTION: SEQ ID NO:3:

```
CACAAATTCT  TCTTTCTTCC  TTACTACTGA  TCATTAATCT  GAAAACAAAA  CCAAACAAAC         60

CATTCAAA ATG ATG TAC AAA ATT TTG TGT CTT TCA TTG TTG GTC GCA GCC               110
         Met Tyr Lys Ile Leu Cys Leu Ser Leu Leu Val Ala Ala
         -16 -15                -10                          -5

GTT GCT CGT GAT CAA GTC GAT GTC AAA GAT TGT GCC AAT CAT GAA ATC                158
Val Ala Arg Asp Gln Val Asp Val Lys Asp Cys Ala Asn His Glu Ile
        -1  1            5                   10

AAA AAA GTT TTG GTA CCA GGA TGC CAT GGT TCA GAA CCA TGT ATC ATT                206
Lys Lys Val Leu Val Pro Gly Cys His Gly Ser Glu Pro Cys Ile Ile
    15              20                  25

CAT CGT GGT AAA CCA TTC CAA TTG GAA GCC GTT TTC GAA GCC AAC CAA                254
His Arg Gly Lys Pro Phe Gln Leu Glu Ala Val Phe Glu Ala Asn Gln
30              35                  40                      45

AAC ACA AAA ACG GCT AAA ATT GAA ATC AAA GCC TCA ATC GAT GGT TTA                302
Asn Thr Lys Thr Ala Lys Ile Glu Ile Lys Ala Ser Ile Asp Gly Leu
                50                  55                      60

GAA GTT GAT GTT CCC GGT ATC GAT CCA AAT GCA TGC CAT TAC ATG AAA                350
Glu Val Asp Val Pro Gly Ile Asp Pro Asn Ala Cys His Tyr Met Lys
            65                  70                  75

TGC CCA TTG GTT AAA GGA CAA CAA TAT GAT ATT AAA TAT ACA TGG AAT                398
Cys Pro Leu Val Lys Gly Gln Gln Tyr Asp Ile Lys Tyr Thr Trp Asn
            80                  85                  90

GTT CCG AAA ATT GCA CCA AAA TCT GAA AAT GTT GTC GTC ACT GTT AAA                446
Val Pro Lys Ile Ala Pro Lys Ser Glu Asn Val Val Val Thr Val Lys
        95                  100                 105

GTT ATG GGT GAT GAT GGT GTT TTG GCC TGT GCT ATT GCT ACT CAT GCT                494
Val Met Gly Asp Asp Gly Val Leu Ala Cys Ala Ile Ala Thr His Ala
110             115                 120                     125

AAA ATC CGC GAT TAAATAAACA AAATTTATTG ATTTTGTAAT CACAAATGAT                    546
Lys Ile Arg Asp

TGATTTTCTT TCCAAAAAAA AAATAAATAA AATTTGGGA AT                                  588
```

( 2 ) INFORMATION FOR SEQ ID NO:4:

( i ) SEQUENCE CHARACTERISTICS:
        ( A ) LENGTH: 146 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Met | Tyr | Lys | Ile | Leu | Cys | Leu | Ser | Leu | Leu | Val | Ala | Ala | Val | Ala |
|-----|-----|-----|-----|-----|-----|-----|-----|-----|-----|-----|-----|-----|-----|-----|-----|
| −16 | −15 | | | | −10 | | | | | | | −5 | | | |

| Arg | Asp | Gln | Val | Asp | Val | Lys | Asp | Cys | Ala | Asn | His | Glu | Ile | Lys | Lys |
| −1 | 1 | | | 5 | | | | | 10 | | | | | | 15 |

| Val | Leu | Val | Pro | Gly | Cys | His | Gly | Ser | Glu | Pro | Cys | Ile | Ile | His | Arg |
| | | | | 20 | | | | 25 | | | | | | 30 | |

| Gly | Lys | Pro | Phe | Gln | Leu | Glu | Ala | Val | Phe | Glu | Ala | Asn | Gln | Asn | Thr |
| | | | 35 | | | | | 40 | | | | | 45 | | |

| Lys | Thr | Ala | Lys | Ile | Glu | Ile | Lys | Ala | Ser | Ile | Asp | Gly | Leu | Glu | Val |
| | | 50 | | | | | 55 | | | | | 60 | | | |

| Asp | Val | Pro | Gly | Ile | Asp | Pro | Asn | Ala | Cys | His | Tyr | Met | Lys | Cys | Pro |
| | 65 | | | | | 70 | | | | | 75 | | | | |

| Leu | Val | Lys | Gly | Gln | Gln | Tyr | Asp | Ile | Lys | Tyr | Thr | Trp | Asn | Val | Pro |
| 80 | | | | | 85 | | | | | 90 | | | | | 95 |

| Lys | Ile | Ala | Pro | Lys | Ser | Glu | Asn | Val | Val | Val | Thr | Val | Lys | Val | Met |
| | | | | 100 | | | | | 105 | | | | | 110 | |

| Gly | Asp | Asp | Gly | Val | Leu | Ala | Cys | Ala | Ile | Ala | Thr | His | Ala | Lys | Ile |
| | | | | 115 | | | | | 120 | | | | | 125 | |

Arg Asp ( 2 ) INFORMATION FOR SEQ ID NO:5:

( i ) SEQUENCE CHARACTERISTICS:
        ( A ) LENGTH: 1072 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 36..1001

( x i ) SEQUENCE DESCRIPTION: SEQ ID NO:5:

```
CGTTTCTTC CATCAAAATT AAAAATTCAT CAAAA ATG AAA TTC GTT TTG GCC              53
                                      Met Lys Phe Val Leu Ala
                                      −98              −95

ATT GCC TCT TTG TTG GTA TTG AGC ACT GTT TAT GCT CGT CCA GCT TCA           101
Ile Ala Ser Leu Leu Val Leu Ser Thr Val Tyr Ala Arg Pro Ala Ser
            −90              −85                  −80

ATC AAA ACT TTT GAA GAA TTC AAA AAA GCC TTC AAC AAA AAC TAT GCC           149
Ile Lys Thr Phe Glu Glu Phe Lys Lys Ala Phe Asn Lys Asn Tyr Ala
        −75              −70                  −65

ACC GTT GAA GAG GAA GAA GTT GCC CGT AAA AAC TTT TTG GAA TCA TTG           197
Thr Val Glu Glu Glu Glu Val Ala Arg Lys Asn Phe Leu Glu Ser Leu
−60              −55                  −50                  −45

AAA TAT GTT GAA GCT AAC AAA GGT GCC ATC AAC CAT TTG TCC GAT TTG           245
Lys Tyr Val Glu Ala Asn Lys Gly Ala Ile Asn His Leu Ser Asp Leu
                −40              −35                  −30

TCA TTG GAT GAA TTC AAA AAC CGT TAT TTG ATG AGT GCT GAA GCT TTT           293
Ser Leu Asp Glu Phe Lys Asn Arg Tyr Leu Met Ser Ala Glu Ala Phe
            −25              −20                  −15

GAA CAA CTC AAA ACT CAA TTC GAT TTG AAT GCC GAA ACA AGC GCT TGC           341
Glu Gln Leu Lys Thr Gln Phe Asp Leu Asn Ala Glu Thr Ser Ala Cys
        −10              −5                   −1   1

CGT ATC AAT TCG GTT AAC GTT CCA TCG GAA TTG GAT TTA CGA TCA CTG           389
Arg Ile Asn Ser Val Asn Val Pro Ser Glu Leu Asp Leu Arg Ser Leu
    5                10                  15                  20

CGA ACT GTC ACT CCA ATC CGT ATG CAA GGA GGC TGT GGT TCA TGT TGG           437
Arg Thr Val Thr Pro Ile Arg Met Gln Gly Gly Cys Gly Ser Cys Trp
```

```
GCT TTC TCT GGT GTT GCC GCA ACT GAA TCA GCT TAT TTG GCC TAC CGT      485
Ala Phe Ser Gly Val Ala Ala Thr Glu Ser Ala Tyr Leu Ala Tyr Arg
            40                  45                  50

AAC ACG TCT TTG GAT CTT TCT GAA CAG GAA CTC GTC GAT TGC GCA TCT      533
Asn Thr Ser Leu Asp Leu Ser Glu Gln Glu Leu Val Asp Cys Ala Ser
        55                  60                  65

CAA CAC GGA TGT CAC GGC GAT ACA ATA CCA AGA GGC ATC GAA TAC ATC      581
Gln His Gly Cys His Gly Asp Thr Ile Pro Arg Gly Ile Glu Tyr Ile
    70                  75                  80

CAA CAA AAT GGT GTC GTT GAA GAA AGA AGC TAT CCA TAC GTT GCA CGA      629
Gln Gln Asn Gly Val Val Glu Glu Arg Ser Tyr Pro Tyr Val Ala Arg
85                  90                  95                  100

GAA CAA CGA TGC CGA CGA CCA AAT TCG CAA CAT TAC GGT ATC TCA AAC      677
Glu Gln Arg Cys Arg Arg Pro Asn Ser Gln His Tyr Gly Ile Ser Asn
                105                 110                 115

TAC TGC CAA ATT TAT CCA CCA GAT GTG AAA CAA ATC CGT GAA GCT TTG      725
Tyr Cys Gln Ile Tyr Pro Pro Asp Val Lys Gln Ile Arg Glu Ala Leu
            120                 125                 130

ACT CAA ACA CAC ACA GCT ATT GCC GTC ATT ATT GGC ATC AAA GAT TTG      773
Thr Gln Thr His Thr Ala Ile Ala Val Ile Ile Gly Ile Lys Asp Leu
        135                 140                 145

AGA GCT TTC CAA CAT TAT GAT GGA CGA ACA ATC ATT CAA CAT GAC AAT      821
Arg Ala Phe Gln His Tyr Asp Gly Arg Thr Ile Ile Gln His Asp Asn
    150                 155                 160

GGT TAT CAA CCA AAC TAT CAT GCC GTC AAC ATT GTC GGT TAC GGA AGT      869
Gly Tyr Gln Pro Asn Tyr His Ala Val Asn Ile Val Gly Tyr Gly Ser
165                 170                 175                 180

ACA CAA GGC GAC GAT TAT TGG ATC GTA CGA AAC AGT TGG GAT ACT ACC      917
Thr Gln Gly Asp Asp Tyr Trp Ile Val Arg Asn Ser Trp Asp Thr Thr
                185                 190                 195

TGG GGA GAT AGC GGA TAC GGA TAT TTC CAA GCC GGA AAC AAC CTC ATG      965
Trp Gly Asp Ser Gly Tyr Gly Tyr Phe Gln Ala Gly Asn Asn Leu Met
            200                 205                 210

ATG ATC GAA CAA TAT CCA TAT GTT GTA ATC ATG TGAACATTTG AAATTGAATA   1018
Met Ile Glu Gln Tyr Pro Tyr Val Val Ile Met
        215                 220

TATTTATTTG TTTTCAAAAT AAAAACAACT ACTCTTGCGA GTATTTTTA CTCG          1072
```

( 2 ) INFORMATION FOR SEQ ID NO:6:

( i ) SEQUENCE CHARACTERISTICS:
( A ) LENGTH: 321 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Met Lys Phe Val Leu Ala Ile Ala Ser Leu Leu Val Leu Ser Thr Val
-98             -95                 -90                 -85

Tyr Ala Arg Pro Ala Ser Ile Lys Thr Phe Glu Glu Phe Lys Lys Ala
        -80                 -75                 -70

Phe Asn Lys Asn Tyr Ala Thr Val Glu Glu Glu Glu Val Ala Arg Lys
    -65                 -60                 -55

Asn Phe Leu Glu Ser Leu Lys Tyr Val Glu Ala Asn Lys Gly Ala Ile
-50                 -45                 -40                 -35

Asn His Leu Ser Asp Leu Ser Leu Asp Glu Phe Lys Asn Arg Tyr Leu
            -30                 -25                 -20

Met Ser Ala Glu Ala Phe Glu Gln Leu Lys Thr Gln Phe Asp Leu Asn
        -15                 -10                 -5
```

```
Ala Glu Thr Ser Ala Cys Arg Ile Asn Ser Val Asn Val Pro Ser Glu
   -1   1                 5                  10

Leu Asp Leu Arg Ser Leu Arg Thr Val Thr Pro Ile Arg Met Gln Gly
 15              20              25                       30

Gly Cys Gly Ser Cys Trp Ala Phe Ser Gly Val Ala Ala Thr Glu Ser
             35              40               45

Ala Tyr Leu Ala Tyr Arg Asn Thr Ser Leu Asp Leu Ser Glu Gln Glu
             50              55              60

Leu Val Asp Cys Ala Ser Gln His Gly Cys His Gly Asp Thr Ile Pro
         65              70              75

Arg Gly Ile Glu Tyr Ile Gln Gln Asn Gly Val Val Glu Glu Arg Ser
         80              85              90

Tyr Pro Tyr Val Ala Arg Glu Gln Arg Cys Arg Arg Pro Asn Ser Gln
 95              100             105                     110

His Tyr Gly Ile Ser Asn Tyr Cys Gln Ile Tyr Pro Pro Asp Val Lys
                 115             120                     125

Gln Ile Arg Glu Ala Leu Thr Gln Thr His Thr Ala Ile Ala Val Ile
             130             135             140

Ile Gly Ile Lys Asp Leu Arg Ala Phe Gln His Tyr Asp Gly Arg Thr
         145             150             155

Ile Ile Gln His Asp Asn Gly Tyr Gln Pro Asn Tyr His Ala Val Asn
         160             165             170

Ile Val Gly Tyr Gly Ser Thr Gln Gly Asp Asp Tyr Trp Ile Val Arg
175              180             185                     190

Asn Ser Trp Asp Thr Thr Trp Gly Asp Ser Gly Tyr Gly Tyr Phe Gln
             195             200             205

Ala Gly Asn Asn Leu Met Met Ile Glu Gln Tyr Pro Tyr Val Val Ile
             210             215             220

Met
```

( 2 ) INFORMATION FOR SEQ ID NO:7:

( i ) SEQUENCE CHARACTERISTICS:
        ( A ) LENGTH: 491 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..390

( x i ) SEQUENCE DESCRIPTION: SEQ ID NO:7:

```
GAT CAA GTC GAT GTT AAA GAT TGT GCC AAC AAT GAA ATC AAA AAA GTA       48
Asp Gln Val Asp Val Lys Asp Cys Ala Asn Asn Glu Ile Lys Lys Val
 1               5                  10                  15

ATG GTC GAT GGT TGC CAT GGT TCT GAT CCA TGC ATA ATC CAT CGT GGT       96
Met Val Asp Gly Cys His Gly Ser Asp Pro Cys Ile Ile His Arg Gly
             20                  25                  30

AAA CCA TTC ACT TTG GAA GCC TTA TTC GAT GCC AAC CAA AAC ACT AAA      144
Lys Pro Phe Thr Leu Glu Ala Leu Phe Asp Ala Asn Gln Asn Thr Lys
         35                  40                  45

ACC GCT AAA ACT GAA ATC AAA GCC AGC CTC GAT GGT CTT GAA ATT GAT      192
Thr Ala Lys Thr Glu Ile Lys Ala Ser Leu Asp Gly Leu Glu Ile Asp
     50                  55                  60

GTT CCC GGT ATT GAT ACC AAT GCT TGC CAT TTT ATG AAA TGT CCA TTG      240
Val Pro Gly Ile Asp Thr Asn Ala Cys His Phe Met Lys Cys Pro Leu
 65                  70                  75                  80

GTT AAA GGT CAA CAA TAT GAT GCC AAA TAT ACA TGG AAT GTG CCC AAA      288
```

| | | | | | | | | | | | | | | | |
|---|---|---|---|---|---|---|---|---|---|---|---|---|---|---|---|
|Val|Lys|Gly|Gln|Gln|Tyr|Asp|Ala|Lys|Tyr|Thr|Trp|Asn|Val|Pro|Lys|
| | | |  |85| | | |90| | | | |  |95|  |

ATT GCA CCA AAA TCT GAA AAC GTT GTC GTT ACA GTC AAA CTT GTT GGT    336
Ile Ala Pro Lys Ser Glu Asn Val Val Val Thr Val Lys Leu Val Gly
            100                 105                 110

GAT AAT GGT GTT TTG GCT TGC GCT ATT GCT ACC CAC GCT AAA ATC CGT    384
Asp Asn Gly Val Leu Ala Cys Ala Ile Ala Thr His Ala Lys Ile Arg
        115                 120                 125

GAT TAAAAAAAAA AAATAAATAT GAAATTTTC ACCAACATCG AACAAAATTC          437
Asp
    130

AATAACCAAA ATTTGAATCA AAAACGGAAT TCCAAGCTGA GCGCCGGTCG CTAC        491

( 2 ) INFORMATION FOR SEQ ID NO:8:

( i ) SEQUENCE CHARACTERISTICS:
        ( A ) LENGTH: 129 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

Asp Gln Val Asp Val Lys Asp Cys Ala Asn Asn Glu Ile Lys Lys Val
 1               5                  10                  15

Met Val Asp Gly Cys His Gly Ser Asp Pro Cys Ile Ile His Arg Gly
            20                  25                  30

Lys Pro Phe Thr Leu Glu Ala Leu Phe Asp Ala Asn Gln Asn Thr Lys
        35                  40                  45

Thr Ala Lys Thr Glu Ile Lys Ala Ser Leu Asp Gly Leu Glu Ile Asp
    50                  55                  60

Val Pro Gly Ile Asp Thr Asn Ala Cys His Phe Met Lys Cys Pro Leu
65                  70                  75                  80

Val Lys Gly Gln Gln Tyr Asp Ala Lys Tyr Thr Trp Asn Val Pro Lys
                85                  90                  95

Ile Ala Pro Lys Ser Glu Asn Val Val Val Thr Val Lys Leu Val Gly
            100                 105                 110

Asp Asn Gly Val Leu Ala Cys Ala Ile Ala Thr His Ala Lys Ile Arg
        115                 120                 125

Asp ( 2 ) INFORMATION FOR SEQ ID NO:9:

( i ) SEQUENCE CHARACTERISTICS:
        ( A ) LENGTH: 1172 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..738

( x i ) SEQUENCE DESCRIPTION: SEQ ID NO:9:

GAATTCCTTT TTTTTTCTTT CTCTCTCTAA AATCTAAAAT CCATCCAAC ATG AAA ATT    58
                                                      Met Lys Ile
                                                          -98

GTT TTG GCC ATC GCC TCA TTG TTG GCA TTG AGC GCT GTT TAT GCT CGT    106
Thr Leu Ala Ile Ala Ser Leu Leu Ala Leu Ser Ala Val Tyr Ala Arg
-95                 -90                 -85                 -80

CCA TCA TCG ATC AAA ACT TTT GAA GAA TAC AAA AAA GCC TTC AAC AAA    154
Pro Ser Ser Ile Lys Thr Phe Glu Glu Tyr Lys Lys Ala Phe Asn Lys

|  |  |  | −75 |  |  |  |  | −70 |  |  |  |  | −65 |  |  |  |
|---|---|---|---|---|---|---|---|---|---|---|---|---|---|---|---|---|
| AGT | TAT | GCT | ACC | TTC | GAA | GAT | CAA | GAA | GCT | GCC | CGT | AAA | AAC | TTT | TTG | 202 |
| Ser | Tyr | Ala | Thr | Phe | Glu | Asp | Gln | Glu | Ala | Ala | Arg | Lys | Asn | Phe | Leu |  |
|  |  |  | −60 |  |  |  |  | −55 |  |  |  |  | −50 |  |  |  |
| GAA | TCA | GTA | AAA | TAT | GTT | CAA | TCA | AAT | GGA | GGT | GCC | ATC | AAC | CAT | TTG | 250 |
| Glu | Ser | Val | Lys | Tyr | Val | Gln | Ser | Asn | Gly | Gly | Ala | Ile | Asn | His | Leu |  |
|  |  |  | −45 |  |  |  |  | −40 |  |  |  |  | −35 |  |  |  |
| TCC | GAT | TTG | TCG | TTG | GAT | GAA | TTC | AAA | AAC | CGA | TTT | TTG | ATG | AGT | GCA | 298 |
| Ser | Asp | Leu | Ser | Leu | Asp | Glu | Phe | Lys | Asn | Arg | Phe | Leu | Met | Ser | Ala |  |
|  |  |  | −30 |  |  |  |  | −25 |  |  |  |  | −20 |  |  |  |
| GAA | GCT | TTT | GAA | CAC | CTC | AAA | ACT | CAA | TTC | GAT | TTG | AAT | GCT | GAA | ACT | 346 |
| Glu | Ala | Phe | Glu | His | Leu | Lys | Thr | Gln | Phe | Asp | Leu | Asn | Ala | Glu | Thr |  |
|  |  |  | −15 |  |  |  |  | −10 |  |  |  |  | −5 |  |  | −1 | 1 |
| AAC | GCC | TGC | AGT | ATC | AAT | GGA | AAT | GCT | CCA | GCT | GAA | ATC | GAT | TTG | CGA | 394 |
| Asn | Ala | Cys | Ser | Ile | Asn | Gly | Asn | Ala | Pro | Ala | Glu | Ile | Asp | Leu | Arg |  |
|  |  |  | 5 |  |  |  |  | 10 |  |  |  |  | 15 |  |  |  |
| CAA | ATG | CGA | ACT | GTC | ACT | CCC | ATT | CGT | ATG | CAA | GGA | GGC | TGT | GGT | TCA | 442 |
| Gln | Met | Arg | Thr | Val | Thr | Pro | Ile | Arg | Met | Gln | Gly | Gly | Cys | Gly | Ser |  |
|  |  |  | 20 |  |  |  |  | 25 |  |  |  |  | 30 |  |  |  |
| TGT | TGG | GCT | TTC | TCT | GGT | GTT | GCC | GCA | ACT | GAA | TCA | GCT | TAT | TTG | GCT | 490 |
| Cys | Trp | Ala | Phe | Ser | Gly | Val | Ala | Ala | Thr | Glu | Ser | Ala | Tyr | Leu | Ala |  |
|  |  |  | 35 |  |  |  |  | 40 |  |  |  |  | 45 |  |  |  |
| CAC | CGT | AAT | CAA | TCA | TTG | GAT | CTT | GCT | GAA | CAA | GAA | TTA | GTC | GAT | TGT | 538 |
| His | Arg | Asn | Gln | Ser | Leu | Asp | Leu | Ala | Glu | Gln | Glu | Leu | Val | Asp | Cys |  |
|  |  |  | 50 |  |  |  |  | 55 |  |  |  |  | 60 |  |  | 65 |
| GCT | TCC | CAA | CAC | GGT | TGT | CAT | GGT | GAT | ACC | ATT | CCA | CGT | GGT | ATT | GAA | 586 |
| Ala | Ser | Gln | His | Gly | Cys | His | Gly | Asp | Thr | Ile | Pro | Arg | Gly | Ile | Glu |  |
|  |  |  |  | 70 |  |  |  |  | 75 |  |  |  |  | 80 |  |  |
| TAC | ATC | CAA | CAT | AAT | GGT | GTC | GTC | CAA | GAA | AGC | TAC | TAT | CGA | TAC | GTT | 634 |
| Tyr | Ile | Gln | His | Asn | Gly | Val | Val | Gln | Glu | Ser | Tyr | Tyr | Arg | Tyr | Val |  |
|  |  |  |  | 85 |  |  |  |  | 90 |  |  |  |  | 95 |  |  |
| GCA | CGA | GAA | CAA | TCA | TGC | CGA | CGA | CCA | AAT | GCA | CAA | CGT | TTC | GGT | ATC | 682 |
| Ala | Arg | Glu | Gln | Ser | Cys | Arg | Arg | Pro | Asn | Ala | Gln | Arg | Phe | Gly | Ile |  |
|  |  |  | 100 |  |  |  |  | 105 |  |  |  |  | 110 |  |  |  |
| TCA | AAC | TAT | TGC | CAA | ATT | TAC | CCA | CCA | AAT | GCA | AAC | AAA | ATT | CGT | GAA | 730 |
| Ser | Asn | Tyr | Cys | Gln | Ile | Tyr | Pro | Pro | Asn | Ala | Asn | Lys | Ile | Arg | Glu |  |
|  |  |  | 115 |  |  |  |  | 120 |  |  |  |  | 125 |  |  |  |
| GCT | TTG | GCT | CAA | ACC | CAC | AGC | GCT | ATT | GCC | GTC | ATT | ATT | GGC | ATC | AAA | 778 |
| Ala | Leu | Ala | Gln | Thr | His | Ser | Ala | Ile | Ala | Val | Ile | Ile | Gly | Ile | Lys |  |
| 130 |  |  |  |  |  |  | 135 |  |  |  |  | 140 |  |  | 145 |  |
| GAT | TTA | GAC | GCA | TTC | CGT | CAT | TAT | GAT | GGC | CGA | ACA | ATC | ATT | CAA | CGC | 826 |
| Asp | Leu | Asp | Ala | Phe | Arg | His | Tyr | Asp | Gly | Arg | Thr | Ile | Ile | Gln | Arg |  |
|  |  |  |  | 150 |  |  |  |  | 155 |  |  |  |  | 160 |  |  |
| GAT | AAT | GGT | TAC | CAA | CCA | AAC | TAT | CAC | GCT | GTC | AAC | ATT | GTT | GGT | TAC | 874 |
| Asp | Asn | Gly | Tyr | Gln | Pro | Asn | Tyr | His | Ala | Val | Asn | Ile | Val | Gly | Tyr |  |
|  |  |  | 165 |  |  |  |  | 170 |  |  |  |  | 175 |  |  |  |
| AGT | AAC | GCA | CAA | GGT | GTC | GAT | TAT | TGG | ATC | GTA | CGA | AAC | AGT | TGG | GAT | 922 |
| Ser | Asn | Ala | Gln | Gly | Val | Asp | Tyr | Trp | Ile | Val | Arg | Asn | Ser | Trp | Asp |  |
|  |  |  | 180 |  |  |  |  | 185 |  |  |  |  | 190 |  |  |  |
| ACC | AAT | TGG | GGT | GAT | AAT | GGT | TAC | GGT | TAT | TTT | GCT | GCC | AAC | ATC | GAT | 970 |
| Thr | Asn | Trp | Gly | Asp | Asn | Gly | Tyr | Gly | Tyr | Phe | Ala | Ala | Asn | Ile | Asp |  |
|  |  |  | 195 |  |  |  |  | 200 |  |  |  |  | 205 |  |  |  |
| TTG | ATG | ATG | ATT | GAA | GAA | TAT | CCA | TAT | GTT | GTC | ATT | CTC | TAAACAAAAA |  |  | 1019 |
| Leu | Met | Met | Ile | Glu | Glu | Tyr | Pro | Tyr | Val | Val | Ile | Leu |  |  |  |  |
| 210 |  |  |  |  | 215 |  |  |  |  | 220 |  |  |  |  |  |  |

GACAATTTCT TATATGATTG TCACTAATTT ATTTAAAATC AAAATTTTTA GAAAATGAAT    1079

AAATTCATTC ACAAAAATTA AAAAAAAAAA AAAAAAAAAA AAAAAAAAAA AAAAAAAAAA    1139

AAAAAAAAAA AAAAAAAAAA AAAAAAAAAA AAA    1172

( 2 ) INFORMATION FOR SEQ ID NO:10:

( i ) SEQUENCE CHARACTERISTICS:
    ( A ) LENGTH: 320 amino acids
    ( B ) TYPE: amino acid
    ( D ) TOPOLOGY: linear ( i i ) MOLECULE TYPE: protein ( x i ) SEQUENCE DESCRIPTION: SEQ ID NO:10:

```
Met Lys Ile Thr Leu Ala Ile Ala Ser Leu Leu Ala Leu Ser Ala Val
-98         -95             -90              -85
Tyr Ala Arg Pro Ser Ser Ile Lys Thr Phe Glu Glu Tyr Lys Lys Ala
        -80              -75              -70
Phe Asn Lys Ser Tyr Ala Thr Phe Glu Asp Glu Ala Ala Arg Lys
 -65              -60              -55
Asn Phe Leu Glu Ser Val Lys Tyr Val Gln Ser Asn Gly Gly Ala Ile
 -50              -45              -40                       -35
Asn His Leu Ser Asp Leu Ser Leu Asp Glu Phe Lys Asn Arg Phe Leu
              -30              -25                       -20
Met Ser Ala Glu Ala Phe Glu His Leu Lys Thr Gln Phe Asp Leu Asn
         -15              -10              -5
Ala Glu Thr Asn Ala Cys Ser Ile Asn Gly Asn Ala Pro Ala Glu Ile
     -1   1              5                   10
Asp Leu Arg Gln Met Arg Thr Val Thr Pro Ile Arg Met Gln Gly Gly
 15              20              25                       30
Cys Gly Ser Cys Trp Ala Phe Ser Gly Val Ala Ala Thr Glu Ser Ala
              35              40                       45
Tyr Leu Ala His Arg Asn Gln Ser Leu Asp Leu Ala Glu Gln Glu Leu
              50              55                       60
Val Asp Cys Ala Ser Gln His Gly Cys His Gly Asp Thr Ile Pro Arg
         65              70              75
Gly Ile Glu Tyr Ile Gln His Asn Gly Val Val Gln Glu Ser Tyr Tyr
     80              85              90
Arg Tyr Val Ala Arg Glu Gln Ser Cys Arg Arg Pro Asn Ala Gln Arg
 95              100             105                      110
Phe Gly Ile Ser Asn Tyr Cys Gln Ile Tyr Pro Pro Asn Ala Asn Lys
             115             120                      125
Ile Arg Glu Ala Leu Ala Gln Thr His Ser Ala Ile Ala Val Ile Ile
         130             135                      140
Gly Ile Lys Asp Leu Asp Ala Phe Arg His Tyr Asp Gly Arg Thr Ile
     145             150             155
Ile Gln Arg Asp Asn Gly Tyr Gln Pro Asn Tyr His Ala Val Asn Ile
 160             165             170
Val Gly Tyr Ser Asn Ala Gln Gly Val Asp Tyr Trp Ile Val Arg Asn
175             180             185                      190
Ser Trp Asp Thr Asn Trp Gly Asp Asn Gly Tyr Gly Tyr Phe Ala Ala
             195             200                      205
Asn Ile Asp Leu Met Met Ile Glu Glu Tyr Pro Tyr Val Val Ile Leu
             210             215                      220
```

( 2 ) INFORMATION FOR SEQ ID NO:11:

( i ) SEQUENCE CHARACTERISTICS:
        ( A ) LENGTH: 222 amino acids
        ( B ) TYPE: amino acid
        ( D ) TOPOLOGY: linear ( i i ) MOLECULE TYPE: protein ( i x ) FEATURE:
        ( A ) NAME/KEY: misc feature ( B ) LOCATION: 50
( D ) OTHER INFORMATION: /label=Xaa is His or Tyr ( i x ) FEATURE:
( A ) NAME/KEY: misc feature
( B ) LOCATION: 81
( D ) OTHER INFORMATION: /label=Xaa is Glu or Lys ( i x ) FEATURE:
( A ) NAME/KEY: misc feature
( B ) LOCATION: 124
( D ) OTHER INFORMATION: /label=Xaa is Ala or Val ( i x ) FEATURE:
( A ) NAME/KEY: misc feature
( B ) LOCATION: 136
( D ) OTHER INFORMATION: /label=Xaa is Ser or Thr ( i x ) FEATURE:
( A ) NAME/KEY: misc feature
( B ) LOCATION: 215
( D ) OTHER INFORMATION: /label=Xaa is Glu or Gln ( x i ) SEQUENCE DESCRIPTION: SEQ ID NO:11:

```
Thr Asn Ala Cys Ser Ile Asn Gly Asn Ala Pro Ala Glu Ile Asp Leu
 1               5                  10                  15
Arg Gln Met Arg Thr Val Thr Pro Ile Arg Met Gln Gly Gly Cys Gly
             20                  25                  30
Ser Cys Trp Ala Phe Ser Gly Val Ala Ala Thr Glu Ser Ala Tyr Leu
         35                  40                  45
Ala Xaa Arg Asn Gln Ser Leu Asp Leu Ala Glu Gln Glu Leu Val Asp
     50                  55                  60
Cys Ala Ser Gln His Gly Cys His Gly Asp Thr Ile Pro Arg Gly Ile
 65                  70                  75                  80
Xaa Tyr Ile Gln His Asn Gly Val Val Gln Glu Ser Tyr Tyr Arg Tyr
                 85                  90                  95
Val Ala Arg Glu Gln Ser Cys Arg Arg Pro Asn Ala Gln Arg Phe Gly
            100                 105                 110
Ile Ser Asn Tyr Cys Gln Ile Tyr Pro Pro Asn Xaa Asn Lys Ile Arg
            115                 120                 125
Glu Ala Leu Ala Gln Thr His Xaa Ala Ile Ala Val Ile Ile Gly Ile
        130                 135                 140
Lys Asp Leu Asp Ala Phe Arg His Tyr Asp Gly Arg Thr Ile Ile Gln
145                 150                 155                 160
Arg Asp Asn Gly Tyr Gln Pro Asn Tyr His Ala Val Asn Ile Val Gly
                165                 170                 175
Tyr Ser Asn Ala Gln Gly Val Asp Tyr Trp Ile Val Arg Asn Ser Trp
            180                 185                 190
Asp Thr Asn Trp Gly Asp Asn Gly Tyr Gly Tyr Phe Ala Ala Asn Ile
        195                 200                 205
Asp Leu Met Met Ile Glu Xaa Tyr Pro Tyr Val Val Ile Leu
210                 215                 220
```

( 2 ) INFORMATION FOR SEQ ID NO:12:

( i ) SEQUENCE CHARACTERISTICS:
( A ) LENGTH: 129 amino acids
( B ) TYPE: amino acid
( D ) TOPOLOGY: linear ( i i ) MOLECULE TYPE: protein ( i x ) FEATURE:
( A ) NAME/KEY: misc feature
( B ) LOCATION: 47
( D ) OTHER INFORMATION: /label=Xaa is Thr or Ser ( i x ) FEATURE:
    ( A ) NAME/KEY: misc feature
    ( B ) LOCATION: 113
    ( D ) OTHER INFORMATION: /label=Xaa is Asp or Asn ( i x ) FEATURE:
    ( A ) NAME/KEY: misc feature
    ( B ) LOCATION: 127
    ( D ) OTHER INFORMATION: /label=Xaa is Ile or Leu ( x i ) SEQUENCE DESCRIPTION: SEQ ID NO:12:

```
Asp Gln Val Asp Val Lys Asp Cys Ala Asn His Glu Ile Lys Lys Val
 1               5                  10                      15

Leu Val Pro Gly Cys His Gly Ser Glu Pro Cys Ile Ile His Arg Gly
                20              25                  30

Lys Pro Phe Gln Leu Glu Ala Val Phe Glu Ala Asn Gln Asn Xaa Lys
            35              40                  45

Thr Ala Lys Ile Glu Ile Lys Ala Ser Ile Asp Gly Leu Glu Val Asp
        50              55              60

Val Pro Gly Ile Asp Pro Asn Ala Cys His Tyr Met Lys Cys Pro Leu
65                  70              75                      80

Val Lys Gly Gln Gln Tyr Asp Ile Lys Tyr Thr Trp Asn Val Pro Lys
                85              90                      95

Ile Ala Pro Lys Ser Glu Asn Val Val Val Thr Val Lys Val Met Gly
            100             105                 110

Xaa Asp Gly Val Leu Ala Cys Ala Ile Ala Thr His Ala Lys Xaa Arg
            115             120                 125

Asp
```

( 2 ) INFORMATION FOR SEQ ID NO:13:

( i ) SEQUENCE CHARACTERISTICS:
        ( A ) LENGTH: 129 amino acids
        ( B ) TYPE: amino acid
        ( D ) TOPOLOGY: linear ( i i ) MOLECULE TYPE: protein ( i x ) FEATURE:
        ( A ) NAME/KEY: misc feature
        ( B ) LOCATION: 11
        ( D ) OTHER INFORMATION: /label=Xaa is Asn or Ser ( i x ) FEATURE:
        ( A ) NAME/KEY: misc feature
        ( B ) LOCATION: 52
        ( D ) OTHER INFORMATION: /label=Xaa is Thr or Ile ( i x ) FEATURE:
        ( A ) NAME/KEY: misc feature
        ( B ) LOCATION: 54
        ( D ) OTHER INFORMATION: /label=Xaa is Ile or Thr ( i x ) FEATURE:
        ( A ) NAME/KEY: misc feature
        ( B ) LOCATION: 76
        ( D ) OTHER INFORMATION: /label=Xaa is Met or Val ( i x ) FEATURE:
        ( A ) NAME/KEY: misc feature
        ( B ) LOCATION: 88
        ( D ) OTHER INFORMATION: /label=Xaa is Ala or Ile ( i x ) FEATURE:
        ( A ) NAME/KEY: misc feature
        ( B ) LOCATION: 111
        ( D ) OTHER INFORMATION: /label=Xaa is Val or Ile ( x i ) SEQUENCE DESCRIPTION: SEQ ID NO:13:

```
Asp Gln Val Asp Val Lys Asp Cys Ala Asn Xaa Glu Ile Lys Lys Val
 1               5                  10                      15
```

```
Met Val Asp Gly Cys His Gly Ser Asp Pro Cys Ile Ile His Arg Gly
            20              25              30
Lys Pro Phe Thr Leu Glu Ala Leu Phe Asp Ala Asn Gln Asn Thr Lys
        35              40              45
Thr Ala Lys Xaa Glu Xaa Lys Ala Ser Leu Asp Gly Leu Glu Ile Asp
    50              55              60
Val Pro Gly Ile Asp Thr Asn Ala Cys His Phe Xaa Lys Cys Pro Leu
65              70              75              80
Val Lys Gly Gln Gln Tyr Asp Xaa Lys Tyr Thr Trp Asn Val Pro Lys
            85              90              95
Ile Ala Pro Lys Ser Glu Asn Val Val Val Thr Val Lys Leu Xaa Gly
            100             105             110
Asp Asn Gly Val Leu Ala Cys Ala Ile Ala Thr His Ala Lys Ile Arg
            115             120             125
Asp
```